United States Patent [19]

Fujii et al.

[11] Patent Number: 4,992,534
[45] Date of Patent: Feb. 12, 1991

[54] 3'-O-,5'-O-DERIVATIVES OF 2'-DEOXY-5-FLUOROURIDINE

[75] Inventors: Setsuro Fujii, Kyoto; Mitsuru Hirohashi, Ootsu; Yoshihito Yamamoto, Ootsu; Yutaka Kojima, Ootsu, all of Japan

[73] Assignee: Otsuka Pharmaceutical Co., Ltd., Tokyo, Japan

[21] Appl. No.: 230,557

[22] Filed: Aug. 10, 1988

[30] Foreign Application Priority Data

Aug. 12, 1987 [JP] Japan .................. 62-202316
Oct. 29, 1987 [JP] Japan .................. 62-274367

[51] Int. Cl.$^5$ .............................. A61K 31/70
[52] U.S. Cl. ........................... 514/50; 514/49; 514/256; 536/23
[58] Field of Search ............. 536/23; 514/50, 49, 514/256

[56] References Cited

U.S. PATENT DOCUMENTS

| 150,407 | 0/0000 | Fujii et al. |  |
|---|---|---|---|
| 225,984 | 0/0000 | Tada et al. |  |
| 4,340,728 | 7/1982 | Endo et al. | 536/23 |
| 4,599,404 | 7/1986 | Fujii et al. | 536/23 |
| 4,757,139 | 7/1988 | Kawaguchi et al. | 536/23 |

FOREIGN PATENT DOCUMENTS 0129984 3/1988 European Pat. Off.

Primary Examiner—Johnnie R. Brown
Assistant Examiner—Gary L. Kunz
Attorney, Agent, or Firm—Armstrong, Nikaido, Marmelstein, Kubovcik & Murray

[57] ABSTRACT

Derivatives of 5-deoxy-fluorouridine are disclosed of formula (1)

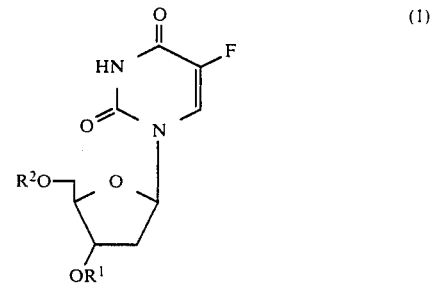

in which one of R and R is a substituted furanylmethyl or thienylmethyl group; and the other R and R is a lower alkanoyl group with one free amino substituent or a salt thereof.

4 Claims, No Drawings

3'-O-,5'-O-DERIVATIVES OF 2'-DEOXY-5-FLUOROURIDINE

This invention relates to novel 2'-deoxy-5fluorouridine derivatives and salts thereof, process for preparing the same and the use thereof, especially for treating cancer.

European Patent Application published on May 14, 1986 under publication number 0 180 897, European Patent Application published on Dec. 2, 1987 under publication number 247381 and British Patent Application published on Jan. 27, 1988 under publication number 2192880 disclose certain 2'-deoxy-5-fluorouridine compounds. These compounds have excellent anti-cancer activities. However, they are not always highly satisfactory in respect of one or more of the properties such as solubility in water, absorption, duration of efficacy, stability, toxicity and the like.

We carried out extensive research in an attempt to improve the antitumor activity of 2'-deoxy-5-fluorouridine and to render it less toxic, and succeeded in synthesizing a class of novel 2'-deoxy-5-fluorouridines in which one of 3'- and 5'-hydrogens is substituted with a furany-lower alkyl or thienyl-lower alkyl group optionally having certain substituent(s) and the other thereof is substituted with a carbonyl group having a specific substituent. We have found that these novel compounds are outstanding in anticancer activities, solubility in water, absorption, long lasting effect, stability and therapeutic index, and low in toxicity and therefore very useful as antitumor agents.

This invention provides a 2'-deoxy-5-fluorouridine derivative of the formula

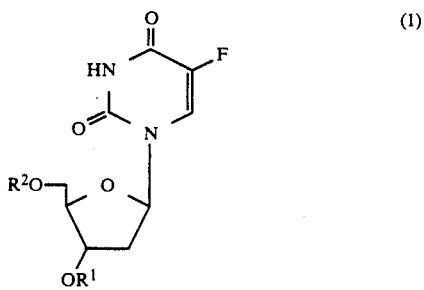

wherein:
one of $R^1$ and $R^2$ is a furanyl-lower alkyl or thienyl-lower alkyl group which may optionally have 1 to 3 substituents selected from the group consisting of carboxyl group, halogen atom and lower alkyl group on the furan or thiophene ring; and the other of $R^1$ and $R^2$ is (i) a lower alkanoyl group which have 1 or 2 substituents selected from the group consisting of a group —$NR^3R^4$ (wherein $R^3$ and $R^4$ each represent a hydrogen atom, lower alkyl group, lower alkoxycarbonyl group or phenyl-lower alkoxycarbonyl group), carboxyl group, lower alkylthio group, phenyl group having a hydroxyl group or phenyl-lower alkoxy group as the substituent on the phenyl ring and phenyl-lower alkoxycarbonyl group, or (ii) a pyrrolidinylcarbonyl group which may optionally have a lower alkoxycarbonyl group, or a salt thereof.

The present invention also provides an anticancer composition comprising an effective amount of a compound of the above formula (1) and a pharmaceutically acceptable carrier therefor.

The present invention further provides a method of treating cancer in a patient comprising administering to said patient an effective amount of a compound of the formula (1).

Throughout the specification and claims, and particularly referring to the general formulas and reaction schemes, typical examples of the groups shown therein are as follows.

Examples of halogen atoms include fluorine atom, chlorine atom, bromine atom, iodine atom and the like.

Examples of lower alkyl groups are alkyl groups having 1 to 6 carbon atoms, such as ethyl, ethyl, propyl, isopropyl, butyl, tert-butyl, pentyl, hexyl and the like.

Examples of furanyl-lower alkyl or thienyl-lower alkyl groups which may optionally have 1 to 3 substituents selected from the group consisting of carboxyl group, halogen atom and lower alkyl group on the furan or thiophene ring include furanyl-$C_1$-$C_6$ alkyl or thienyl-$C_1$-$C_6$ alkyl groups which may optionally have 1 to 3 substituents selected from the group consisting of carboxyl group, halogen atom and $C_1$-$C_6$ alkyl group on the furan or thiophene ring, such as 2-furanylmethyl, 3-furanylmethyl, 2-(2-furanyl)ethyl, 2-(3-furanyl)ethyl, 3-(2-furanyl)propyl, 1-methyl-2-(2-furanyl)ethyl, 4-(2-furanyl)butyl, 5-(2-furanyl)pentyl, 6-(2-furanyl)hexyl, 2-thienylmethyl, 3-thienylmethyl, 2-(2-thienyl)ethyl, 3-(2-thienyl)propyl, 1-methyl-2-(2-thienyl)propyl, 4-(2-thienyl)butyl, 1,1-dimethyl-2-(2-thienyl)ethyl, 5-(2-thienyl)pentyl, 6-(2-thienyl)hexyl, 3-(3-thienyl)propyl, 6-(3-thienyl)hexyl, (5-chloro-2-furanyl)methyl, (4-chloro-2-furanyl)methyl, (3-chloro-2-furanyl)methyl, (4,5-dichloro-2-furanyl)methyl, (3,5-dichloro-2-furanyl)methyl, (3,4,5-trichloro-2-furanyl)methyl, (5-bromo-2-furanyl)methyl, (4-bromo-2-furanyl)methyl, (3-bromo-2-furanyl)methyl, (4,5 dibromo-2-furanyl)methyl, (2,5-dibromo-3-furanyl)methyl, (3,4,5-tribromo-2-furanyl)methyl, (5-fluoro-2-furanyl)methyl, (3-fluoro-2-furanyl)methyl, (4,5-difluoro-2-furanyl)methyl, (4-iodo-2-furanyl)methyl, (5-iodo-3-furanyl)methyl, (3,4,5-triiodo-2-furanyl)methyl, 2-(4-chloro-2-furanyl)ethyl, 3-(3-bromo-2-furanyl)propyl, 1-methyl-2-(5-fluoro-2-furanyl)propyl, 5-(4,5-dichloro-2-furanyl)pentyl, 6-(5-chloro-3-furanyl)hexyl, (5-methyl-2-furanyl)methyl, (4-ethyl-2-furanyl)methyl, (3-propyl-2-furanyl)methyl, (2-butyl-3-furanyl)methyl, (5-t-butyl-2-furanyl)methyl, (4-pentyl-2-furanyl)methyl, (5-hexyl-3-furanyl)methyl, (3,5-dimethyl-2-furanyl)methyl, (3,4,5-trimethyl-2-furanyl)methyl, 2-(5-methyl-2-furanyl)ethyl, 3-(3-ethyl-2-furanyl)propyl, 1,1-dimethyl-2-(4,5-dimethyl-2-furanyl)ethyl, 4-(4-ethyl-2-furanyl)butyl, 5-(5-propyl-2-furanyl)pentyl, 6-(5-methyl-3-furanyl)hexyl, (5-carboxy-2-furanyl)methyl, (5-carboxy-3-furanyl)methyl, (5-chloro-2-thinyl)methyl, (4-chloro-2-thienyl)methyl, (3-chloro-2-thienyl)methyl, (4,5-dichloro-2-thienyl)methyl, (3,4-dichloro-2thienyl)methyl, (3,4,5-trichloro-2-thienyl)-methyl, (5-bromo-2-thienyl)methyl, (4-bromo-2-thienyl)-methyl, (3-bromo-2-thienyl)methyl, (3,5-dibromo-2-thienyl)methyl, (4,5-dibromo-2-thienyl)methyl, (3,4,5-tribromo-2-thienyl)-methyl, (5-fluoro-3-thienyl)methyl, (4-fluoro-2-thienyl)-methyl, (3,5-difluoro-2-thienyl)methyl, (5-iodo-3-thienyl)methyl, (3-iodo-3-thienyl)methyl, 2-(4,5-diiodo-2-thienyl)ethyl, 3-(3-bromo-2-thienyl)propyl, 1,1-dimethyl-2(4-chloro-2-thienyl)ethyl, 4-(5-chloro-3-thienyl)butyl, 5-(4,5-dibromo-2-thienyl)pentyl, 6-(5-bromo-2-thienyl)hexyl, (5-methyl-2-thienyl)methyl, (4- ethyl-2-thienyl)methyl, (5-propyl-2-thienyl)methyl, (3-butyl-2-thienyl)methyl, (5-t-butyl-2-thienyl)methyl, (4-pentyl-2-thienyl)methyl, (5-hexyl-3-thienyl)methyl, (3,5-dimethyl-2-thienyl)methyl, (4,5-diethyl-2-thienyl)methyl, (3,4,5-trimethyl-2-thienyl)methyl, 2-(5-ethyl-2-thienyl)ethyl, 3-(3-methyl-2-thienyl)propyl, 1,1-dimethyl-2-(5-ethyl-2-thienyl)ethyl, 4-(3,5-dimethyl-2-thienyl)butyl, 5-(5-ethyl-2-thienyl)pentyl, 6-(5-methyl-3-thienyl)hexyl, (5-carboxy-2-thienyl)methyl, (5-carboxy-3-thienyl)methyl, and the like.

Examples of lower alkoxycarbonyl groups are alkoxycarbonyl groups wherein the alkoxy moiety has 1 to 6 carbon atoms, such as methoxycarbonyl, ethoxycarbonyl, isopropoxycarbonyl, n-butoxycarbonyl, tert-butoxycarbonyl, pentyloxycarbonyl, hexyloxycarbonyl and the like.

Examples of phenyl-lower alkoxycarbonyl groups are phenylalkoxycarbonyl groups wherein the alkoxy moiety has 1 to 6 carbon atoms, such as benzyloxycarbonyl, 2-phenylethoxycarbonyl, 3-phenylpropoxycarbonyl, 1,1-dimethyl-2-phenylethoxycarbonyl, 4-phenylbutoxycarbonyl, 2-phenylpentyloxycarbonyl, 6-phenylhexyloxycarbonyl and the like.

Examples of lower alkylthio groups are $C_1$-$C_6$ alkylthio groups such as methylthio, ethylthio, propylthio, isopropylthio, butylthio, tert-butylthio, pentylthio, hexylthio and the like.

Examples of phenyl groups having a hydroxyl group or phenyl-lower alkoxy group as the substituent on the phenyl ring are phenyl groups having a hydroxyl group or phenyl-$C_1$-$C_6$ alkoxy group as the substituent on the phenyl ring, such as 2-hydroxyphenyl, 3-hydroxyphenyl, 4-hydroxyphenyl, 2-benzyloxyphenyl, 3-benzyloxyphenyl, 4-benzyloxyphenyl, 2-(2-phenylethoxy)phenyl, 3-(3-phenylpropoxy)phenyl, 4-(1,1-dimethyl-2-phenylethoxy)phenyl, 2-(4-phenylbutoxy)phenyl, 3-(5-phenylpentyloxy)phenyl, 4-(6-phenylhexyloxy)phenyl, 4-(2-methyl-3-phenylbutoxy)phenyl and the like.

Examples of lower alkanoyl groups are $C_1$-$C_6$ alkanoyl groups such as formyl, acetyl, propanoyl, butanoyl, 2-methylpropanoyl, pentanoyl, 3-methylpentanoyl, hexanoyl and the like.

Examples of pyrrolidinylcarbonyl groups which may optioanlly have a lower alkoxycarbonyl group are pyrrolidinylcarbonyl groups which may optionally have a ($C_1$-$C_6$ alkoxy)carbonyl group, such as 1-pyrrolidinylcarbonyl, 2-pyrrolidinylcarbonyl, 3-pyrrolidinylcarbonyl, (1-methoxycarbonyl-2-pyrrolidinyl)carbonyl, (1-ethoxycarbonyl-3-pyrrolidinyl)carbonyl, (1-isopropoxycarbonyl-2-pyrrolidinyl)carbonyl, (2-n-butoxycarbonyl-3-pyrrolidinyl)carbonyl, (1-tert-butoxycarbonyl-2-pyrrolidinyl)carbonyl, (3-pentyloxycarbonyl-2-pyrrolidinyl)carbonyl, (1-hexyloxycarbonyl-2-pyrrolidinyl)carbonyl, (3-methoxycarbonyl-1-pyrrolidinyl)carbonyl and the like.

Examples of lower alkylene groups are $C_1$-$C_6$ alkylene groups such as methylene, ethylene, trimethylene, 1-methylethylene, tetramethylene, 2-methyltrimethylene, pentamethylene, hexamethylene and the like.

A preferred class of compounds are the compounds of the formula (1) wherein one of $R^1$ and $R^2$, especially $R^1$, is a thienyl-lower alkyl group which may optionally have 1 to 3 substituents selected from the group consisting of carboxyl group, halogen atom and lower alkyl group on the thiophene ring, especially a thienyl-lower alkyl group which has 1 to 3 halogen atoms on the thiophene ring. In this case, it is preferable that $R^2$ is either (a) a lower alkanoyl group which has 1 or 2 groups of the formula —$NR^3R^4$ (wherein $R^3$ and $R^4$ each represent a hydrogen atom or lower alkyl group) or pyrrolidinylcarbonyl group, in particular a lower alkanoyl group which has one —$NH_2$ group, or (b) a lower alkanoyl group which has 1 or 2 carboxyl groups.

Another prefered class of compounds are the compounds of the formula (1) wherein $R^1$ is a furanyl-lower alkyl group which may have 1 to 3 substituents selected from the group consisting of carboxyl group, halogen atom and lower alkyl group on the furan ring, particularly a furanyl-lower alkyl group which has 1 to 3 halogen atoms on the furan ring. In this case, $R^2$ is preferably a lower alkanoyl group having one —$NH_2$ group.

The compound of the formula (1) according to the present invention can be prepared by the process shown below in Reaction Scheme 1 or 2.

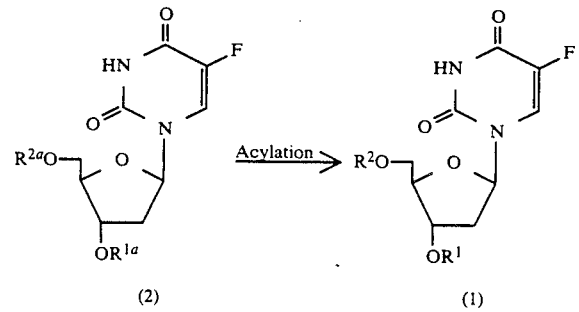

In the above formulas, $R^1$ and $R^2$ are as defined above, and one of $R^{1a}$ and $R^{2a}$ is a hydrogen atom while the other is a furanyl-lower alkyl or thienyl-lower alkyl group which may optionally have 1 to 3 substituents selected from the group consisting of carboxyl group, halogen atom and lower alkyl group on the furan or thiophene ring.

According to the reaction illustrated above, the compound of the formula (1) of the invention (hereinafter referred to as "compound (1)") can be prepared by acylation of free hydroxyl group of the compound of the formula (2) (hereinafter referred to as "compound (2)"). The acyl group to be introduced by this acylation includes (i) a lower alkanoyl group which have 1 to 2 substituents selected from the group consisting of a group —$NR^3R^4$ ($R^3$ and $R^4$ each represent a hydrogen atom, lower alkyl group, lower alkoxycarbonyl group or phenyl-lower alkoxycarbonyl group), carboxyl group, lower alkylthio group, phenyl group having a hydroxyl group or phenyl-lower alkoxy group as the substituent on the phenyl ring and phenyl-lower alkoxycarbonyl group, or (ii) a pyrrolidinylcarbonyl group which may optionally have a lower alkoxycarbonyl group. This acylation reaction can be carried out by any of usual acylation methods such as an acid anhydride method mixed acid anhydride method, N,N'-dicyclohexylcarbodiimide method (DCC method), acid halide method, etc.

(A) The acid anhydride method is practiced by causing the compound (2) to react with an acid anhydride in a suitable solvent This method employs as the acid anhydride the anhydride of an acid corresponding to the acyl group to be introduced. When the acyl group is a lower alkanoyl group having a carboxyl group, it is preferred to use an intramolecular acid anhydride represented by the formula

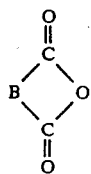

wherein B is a lower alkylene group.

It is suitable to use the acid anhydride in an amount of at least about 1 mole, preferably about 1 to about 4 moles, per mole of the compound (2). Useful solvents are, for example, inert solvents including halogenated hydrocarbons such as dichloromethane, chloroform, carbon tetrachloride and the like, ethers such as dioxane, tetrahydrofuran, diethyl ether and the like, ketones such as acetone, methyl ethyl ketone and the like, acetonitrile, ethyl acetate, dimethylformamide, dimethylsulfoxide, pyridine, etc. It is preferable that these solvents are anhydrous. The reaction is conducted at a temperature of usually about 0° to about 100° C., preferably around room temperature to about 60° C., and is completed in about 20 minutes to about 3 hours. The reaction is advantageously performed in the presence of a basic compound. Examples of useful basic compounds are organic basic compounds such as pyridine, triethylamine, N,N-dimethylaniline and like tertiary amines, etc. and inorganic basic compounds such as potassium carbonate, sodium hydrogencarbonate, sodium acetate, potassium hydroxide and the like.

(B) The mixed acid anhydride method can be conducted under the same reaction conditions as those for the acid anhydride method except that the reaction temeprature is usually about −30° to about 60° C., preferably about −15° to 0° C. Usable as the mixed acid anhydride are compounds prepared by reacting a carboxylic acid compound corresponding to the acyl group to be introduced with other acid halide compound such as preferably isobutyloxycarbonyl halide, ethoxycarbonyl halide or like lower alkoxycarbonyl halides, 2,4,6-triisopropylbenzenesulfonyl halide or the like.

(C) The DCC method is practiced by causing the compound (2) to react with an acid compound correponding to the acyl group to be introduced in the presence of a dehydrating agent in a suitable solvent The acid compound is used in an amount of at least about 1 mole, preferably about 1 to 4 moles, per mole of the compound (2). Examples of useful solvents are inert solvents including halogenated hydrocarbons such as dichloromethane, chloroform, carbon tetrachloride and the like, ethers such as dioxane, tetrahydrofuran, diethyl ether and the like, ketones such as acetone, methyl ethyl ketone and the like, acetonitrile, ethyl acetate, dimethylformamide, dimethylsulfoxide, etc. which are preferably anhydrous. The reaction is conducted at a temperature of about 0° C. to around room temperature and is completed in about 20 minutes to about 30 hours. Examples of dehydrating agents useful in the reaction are dicyclohexylcarbodiimide, 1-ethyl-3-(3-dimethylaminopropyl)carbodiimide, 1-cyclohexyl-3-(2-morpholinoethyl)-carbodiimide, etc.

(D) The acid halide method is carried out by reacting the compound (2) with an acyl halide having an acyl group to be introduced in the presence of an an acid scavenger in a suitable solvent Examples of the halogen atoms of acyl halide are fluorine, chlorine, bromine, iodine, etc. The acyl halide is used in an amount of about 1 mole per mole of the compound (2). Usable as the solvent are the same inert solvents as those used in the acid anhydride method noted above. The reaction is conducted at a temperature of usually about −10° to about 100° C., preferably around 0° C. to room temperature, and is completed in about 2 minutes to about 3 hours. Useful acid scavengers include, for example, the same basic compounds as used in the acid anhydride method.

When the acyl group to be introduced in the process as shown above in Reaction Scheme-1 is a group having a nitrogen atom, such as an amino group (—NH$_2$) or imino group (>NH), hydroxyl group or carboxyl group capable of participating in the reaction, it is desired to effect the acylation using a compound with such nitrogen atom, hydroxyl group or carboxyl group protected with a suitable protective group, followed by a reaction for removing the protective group from the compound thus obtained. Examples of protective groups for the nitrogen atom are a lower alkoxycarbonyl group or phenyl-lower alkoxycarbonyl group. A phenyl-lower alkyl group is usable as the protective group for the hydroxyl or carboxyl group. Exemplary of the phenyl-lower alkyl group are phenyl-alkyl groups having an alkyl moiety with 1 to 6 carbon atoms such as benzyl, 2-phenylethyl, 3-phenylpropyl, 2-methyl-3-phenylbutyl, 4-phenylbutyl, 5-phenylpentyl, 6-phenylhexyl, etc.

The reaction for removal of the protective group can be carried out by suitable methods commonly employed for such reaction, e.g. using an appropriate amount of an acid usually in a solvent. Examples of useful acids are inorganic acids such as hydrogen chloride, hydrogen bromide, hydrogen fluoride, sulfuric acid, perchloric acid and the like; organic acids including lower alkanoic acids such as formic acid, acetic acid, trifluoroacetic acid, chloroacetic acid, propionic acid and the like, benzoic acid, organic sulfonic acids such as methanesulfonic acid, ethanesulfonic acid, benzenesulfonic acid, 4-methylbenzenesulfonic acid and the like. Examples of useful solvents are usual inert solvents including water; lower alcohols such as methanol, ethanol, isopropanol and the like; ketones such as acetone, methyl ethyl ketone and the like; ethers such as diethyl ether, tetrahydrofuran, dioxane and the like; esters such as methyl acetate, ethyl acetate and the like; aromatic hydrocarbons such as benzene, toluene, xylene, chlorobenzene and the like; lower alkanoic acids such as acetic acid, propionic acid and the like; dimethylsulfoxide, dimethylacetamide, dimethylformamide and the like; mixtures thereof; etc. The reaction temperature is not specifically limited but can be suitably determined over a wide range. It is usually about 0° to about 100° C., preferably around room temperature to about 80° C. The reaction is completed in about 3 minutes to about 20 hours. The amount of the acid used is usually 2 equivalents to an excess amount, preferably an excess amount.

When the protective group is benzyloxycarbonyl or benzyl, the protective group can also be removed by a catalytic reduction method This method can be practiced by hydrogenation in a suitable solvent in the presence of a catalyst such as palladium-carbon, palladium-black, palladium-barium sulfate, palladium-barium carbonate, platinum oxide, Raney-nickel, etc. The amount of the catalyst is not specifically limited but is usually about 1 to about 10% by weight based on the starting compound Useful solvents are for example, ethers such as tetrahydrofuran, dioxane and the like; alcohols such as methanol, ethanol, isoproanol and the like; esters such as methyl acetate, ethyl acetate and the like; water; acetic acid; dimethylformamide, dimethylacetamide and the like; mixtures thereof; etc.

When the reaction solution contains a mineral acid such as hydrochloric acid, sulfuric scid, phosphoric acid, perchloric acid or the like or an organic acid such as acetic acid, tartaric acid, citric acid, fumaric acid, methanesulfonic acid, p-toluenesulfonic acid or the like, a corresponding salt of the compound (1) can be obtained The reaction for removal of the lower alkoxycarbonyl group (protective group-removing reaction) can be performed also by causing an iodotrimethylsilane to react in a suitable solvent according to the process described in known publication (Journal of the Chemical Society, Chemical Communication 495 (1979). Illustrative of useful solvents are inert solvents such as chloroform, dichloromethane and like halogenated hydrocarbons, dioxane, tetrahydrofuran and like ethers, benzene, toluene and like aromatic hydrocarbons, dimethylformamide, acetonitrile, etc. The reaction is carried out at a temperature of usually about −20° to about 50° C., preferably about 0° C. to room temperature an is completed in 5 minutes to about 10 hours. The amount of the iodotrimethylsilane used is usually about 1.0 mole, preferably about 1.0 to about 1.2 moles, per mole of the protected reactant.

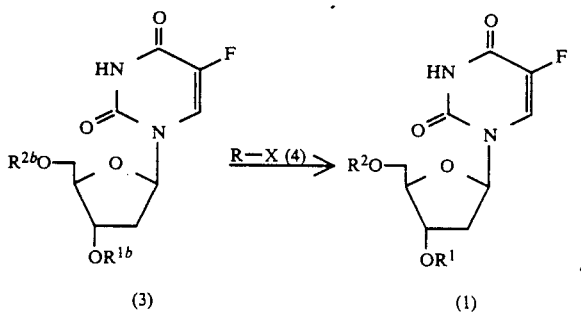

In the above formulas, X is a halogen atom, R is a furanyl-lower alkyl group or thienyl-lower alkyl group which may have 1 to 3 substituents selected from the group consisting of carboxyl group, halogen atom and lower alkyl group on the furan or thiophene ring, one of $R^{1b}$ and $R^{2b}$ is a hydrogen atom while the other is (i) a lower alkanoyl group which have 1 to 2 substituents selected from the group consisting of a group —NR$^3$R$^4$ (R$^3$ and R$^4$ each represent a hydrogen atom, lower alkyl group, lower alkoxycarbonyl group or phenyl-lower alkoxycarbonyl group), carboxyl group, lower alkylthio group, phenyl group having a hydroxyl group or phenyl-lower alkoxy group as the substituent on the phenyl ring and phenyl-lower alkoxycarbonyl group, or (ii) a pyrrolidinylcarbonyl group which may optionally have a lower alkoxycarbonyl group, and R$^1$ and R$^2$ are as defined above.

In the process as shown above, the reaction between the compound of the formula (3) (hereinafer referred to as "compound (3)") and the compound of the formula (4) (hereinafter referred to as "compound (4)"), namely the reaction for introduction of the R group, is carried out under the conditions for usual dehydrohalogenation reaction. Useful dehydrohalogenating agents can be any of basic compounds commonly used for this type of reaction, such as sodium hydroxide, potassium hydroxide, sodium carbonate, potassium carbonate, sodium hydrogencabonate, potassium hydrogencarbonate, sodium, potassium and like alkali metals, sodium hydride, potassium hydride and like alkali metal hydrides, etc.

The foregoing reaction can be effected in the presence or in the absence of a solvent. Useful solvents can be any of usual inert solvents Among them, it is advantageous to use tetrahydrofuran, dioxane and like ethers, benzene, toluene, xylene, chlorobenzene and like aromatic hydrocarbons, acetone, methyl ethyl ketone and like ketones, acetonitrile, propionitrile and like nitriles, dimethylsulfoxide, dimethylacetamide, dimethylformamide, etc.

The amounts of the compound (3) and the compound (4) used are not specifically limited and can be suitably determined over a wide range. The latter is used in an amount of usually at least about 1 mole, preferably about 1 to about 5 moles, per mole of the former. The reaction temperature is not specifically limitative and can be selected from a wide range. It is usually about 0° to about 100° C., preferably room temperature to about 80° C. The reaction is completed in usually about 30 minutes to about 64 hours, preferably about 1 to about 5 hours When the groups represented by $R^{1b}$ and R2b in the process of Reaction Scheme-2 are a nitrogen atom, hydroxyl group or carboxyl group capable of participating in the reaction, it is preferred to conduct the dehydrohalogenation reaction using a compound with the nitrogen atom, hydroxyl group or carboxyl group protected with such protective group as defined in Reaction Scheme-1, followed by a reaction for removal of the protective group.

The reaction for removal of the protective group is conducted in the same manner as shown above in Reaction Scheme-1.

Of the compounds (1) of the invention obtained in Reaction Scheme-1 or -2, the compounds having a nitrogen atom, hydroxyl group or carboxyl group capable of participating in the reaction can be converted into the compound of the invention having the group protected with the protective group by performing, for example, the usual reaction for introduction of protective group to be described later. The compound (2) or (3) to be used as the starting compound in Reaction Scheme-1 or -2 is novel and can be prepared, for example, by the process as illustrated below in Reaction Scheme-3 or -4.

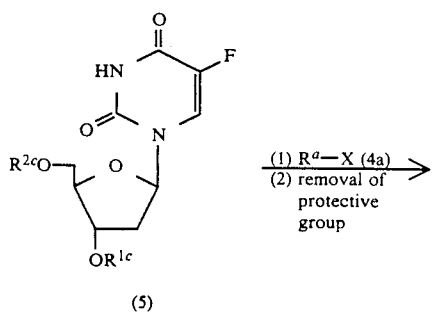

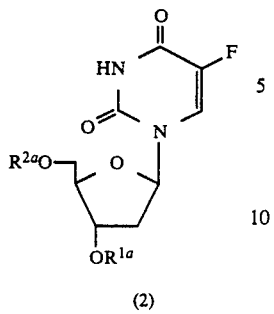

(2)

In the above formulas, $R^{1a}$, R2a and X are as defined above, one of $R^{1c}$ and R2c is a hydrogen atom while the other is a protective group for hydroxyl group or a hydrogen atom, and $R^a$ is a furanyl-lower alkyl group or a thienyl-lower alkyl group which may optionally have 1 to 3 substituents selected from the group consisting of lower alkoxycarbonyl group, halogen atom and lower alkyl group on the furan or thiophene ring.

The protective groups for protecting the hydroxyl group at the 3'- or 5'-position of the sugar moiety include the following. (A) Triaryl-substituted methyl groups represented by the formula

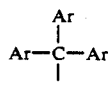

(A)

wherein Ar is an aryl group. Examples of the group of the formula (A) are methyl groups substituted with three aryl groups such as phenyl groups which may optionally have a halogen atom, nitro group, lower alkyl group or lower alkoxy group as the substituent.

(B) Cyclic ether residue groups represented by the formula

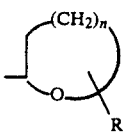

(B)

wherein R' is a hydrogen atom or lower alkyl group and n is 2 or 3. Examples of this group are 2-tetrahydrofuranyl, 2-tetrahydropyranyl, etc.

(C) Tri-lower alkylsilyl groups such as trimethylsilyl, t-butyldimethylsilyl, etc.

(D) Benzyl groups.

The compound of the formula (5) (hereinafter referred to as "compound (5)") having any of the protective groups as exemplified above can be prepared, for example, by reacting the corresponding compound in which $R^{1c}$ and R2C are both hydrogen atoms with a suitable reagent for introducing the protective group.

Usable as the reagent for introducing the protective group are a triaryl-substituted methyl halide capable of producing the protective group of the formula (A), an unsaturated cyclic ether capable of producing the protective group of the formula (B) and represented by the formula

wherein R' and n are as defined in the formula (B), a trilower alkylsilyl halide and a benzyl halide capable of producing the protective group under item (D).

The reaction for introducing the protective group using any of the above halides can be carried out in the same manner as in the dehydrohalogenation reaction shown above in Reaction Scheme-2. The amount of the halide used is about 1 to about 2 moles, preferably about 1 to about 1.5 moles, per mole of the starting compound The reaction is conducted at a temperature of about −30° to about 80° C.

The reaction for introducing the protective group using the unsaturated cyclic ether of the formula (B') is conducted, for example, in the presence of an acid catalyst in an aprotic inert solvent such as tetrahydrofuran, dioxane, acetonitrile or the like Examples of useful acid catalysts are hydrogen bromide, hydrogen chloride and like hydrohalogenic acid, aluminum chloride, boron fluoride, zinc chloride and like Lewis acids, etc. The reaction is carried out using the reagent in an amount of about 1 to about 1.5 moles per mole of the starting compound at a temperature of about −30° to about 60° C. and is completed in about 2 to about 5 hours.

In Reaction Scheme-3, the starting compound (2) of the invention is prepared by causing the compound (5) to react with the halide compound (4a) to introduce the group $R^a$, followed, when required, by a reaction for removing the protective group at the 3'- or 5'-position.

The reaction for introducing the group $R^1$ is conducted under the same conditions as described above in Reaction Scheme-2.

When the compound obtained by the foregoing reaction has a protective group at the 3'- or 5'-position, subsequent reaction for removing the protective group gives the contemplated compound (2). The reaction for removal of the protective group is usually performed using a suitable amount of a catalyst commonly used for usual acid hydrolysis in a solvent. Examples of proper catalysts are inorganic acids such as hydrochloric acid, sulfuric acid, perchloric acid and the like; lower alkanoic acids such as formic acid, acetic acid, propionic acid and the like; organic acids such as benzoic acid, methanesulfonic acid, ethanesulfonic acid, benzenesulfonic acid, 4-methylbenzenesulfonic acid and like organic sulfonic acids; etc. Examples of useful solvents are usual inert solvents including water; lower alcohols such as methanol, ethanol, isopropanol and the like; ketones such as acetone, methyl ethyl ketone and the like; ethers such as diethyl ether, tetrahydrofuran, dioxane and the like; aromatic hydrocarbons such as benzene, toluene, xylene, chlorobenzene and the like; lower alkanoic acids such as acetic acid, propionic acid and the like; dimethylsulfoxide, dimethylacetamide, dimethylformamide and the like; mixtures thereof; etc. The reaction temperature is not specifically limited but can be suitably determined over a wide range. It is usually about 0° to about 100° C., preferably around room temperature to about 80° C. The reaction is completed in about 3 minutes to about 20 hours. The acid is used in a catalytic amount to an excess amount, preferably an excess amount. When the protective group is a benzyl group, the benzyl group can be removed also by usual catalytic reduction method. Useful catalysts include, for example, platinum oxide, palladium-carbon, palladium-black, palladium-barium sulfate, palladium-barium carbonate, Raney-nickel, etc. The catalytic reduction method can be conducted by hydrogenation in the presence of such catalyst. The amount of the catalyst used is not specifically limited but is usually about 5 to about 15% by weight based on the starting compound Useful solvents are, for example, usual inert solvents including lower alcohols such as methanol, ethanol, isopropanol and the like; ethers such as diethyl ether, tetrahydrofuran, dioxane and the like; esters such as methyl acetate, ethyl acetate and the like; lower alkanoic acids such as acetic acid, propionic acid and the like; dimethylformamide, dimethylacetamide and the like; mixtures thereof; etc.

When the reaction is conducted under the conditions for de-esterification in Reaction Scheme-3 the group, among the $R^a$ groups, which has a lower alkoxycarbonyl group may be converted into the corresponding carboxyl group by the resulting deesterification of the ester group.

Of the compounds (2), the compound wherein the group $R^a$ has a lower alkoxycarbonyl group is converted into a compound with the corresponding carboxyl group by usual de-esterification.

The foregoing de-esterification reaction is carried out in the presence of a catalyst for hydrolysis in the presence of a suitable solvent such as dioxane, tetrahydrofuran or like ether, methanol, ethanol or like lower alcohol, water or the like at room temperature to about 100° C. for 30 minutes to 6 hours. Examples of useful catalysts for hydrolysis are basic compounds such as sodium hydroxide, potassium hydroxide and like metal hydroxides, potassium carbonate, sodium carbonate, sodium hydrogencarbonate and like alkali metals carbonate <Reaction Scheme-4>

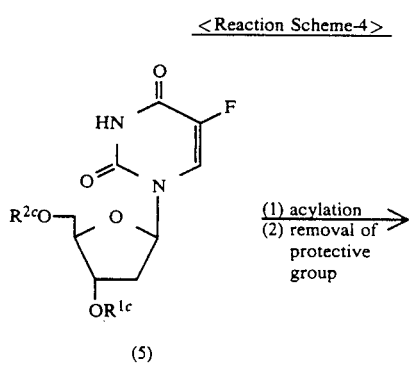

(5)

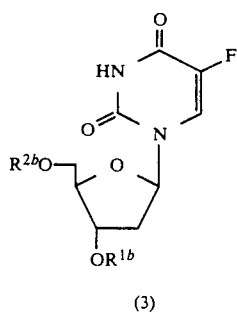

(3)

In the above formulas, $R^{1b}$, $R^{2b}$, $R^{1c}$ and $R^{2c}$ are as defined above. The acylation of the compound of the formula (5) (hereinafter referred to as "compound (5)") in Reaction Scheme-4 can be practiced in the same manner as in the acylation of the compound (2) in Reaction Scheme-1 It is preferred to conduct the acylation of the compound (5) using an acid anhydride corresponding to the acyl group to be introduced in an amount of about 1 to about 1.5 moles per mole of the compound (5) in the same inert solvent as used in Reaction Scheme-1 at about −30° to about 80° C. for about 1 to about 6 hours.

When the acyl group to be introduced has a nitrogen atom, hydroxyl group or carboxyl group capable of participating in the reaction, it is desirable to protect the nitrogen atom, hydroxyl group or carboxyl group by the same procedure as detailed above in Reaction Scheme-1 before acylation.

When the compound thus obtained has a protective group for hydroxyl group at the 3'- or 5'-position, the desired compound (3) can be prepared by performing the reaction for removal of the protective group in a conventional manner. The reaction for removal of the hydroxyl-protecting group can be selectively conducted by using the weakly acidic catalyst to be used in the foregoing reaction for removing the nitrogen-protecting group, or by hydrogenation.

Of the 2'-deoxy-5-fluorouridine derivatives of the formula (1), the compound having a basic group can be easily converted into an acid addition salt by causing a pharmaceutically acceptable acid to act on the compound Examples of useful acids are inorganic acids such as hydrochloric acid, sulfuric acid, phosphoric acid, hydrobromic acid, nitric acid and the like and organic acids such as oxalic acid, maleic acid, fumaric acid, malic acid, tartaric acid, citric acid, benzoic acid 4-methylbenzenesulfonic acid, methanesulfonic acid and the like.

Of the 2'-deoxy-5-fluorouridine derivatives of the formula (1), the compound having an acidic group can be easily made into a salt thereof by causing a pharmaceutically acceptable basic compound to act on the compound. Examples of the basic compound are sodium hydroxide, potassium hydroxide, calcium hydroxide, sodium carbonate, potassium hydrogencarbonate, etc.

The end compound prepared in each step and the compound of the present invention thus obtained can be separated from the reaction product by conventional methods, followed by purification. Useful separation methods and purification methods include extraction with solvent, reprecipitation method, recrystallization method, column chromatography, preparative thin layer chromatography, ion-exchange column chromatography, gel chromatography, affinity chromatography, etc.

The compounds of the invention include all possible optical isomers and stereoisomers.

All of the compounds of the invention and salts thereof thus obtained have an outstanding anticancer effect and are low in toxicity For example, such side effects as reduction in body weight are not observed The compounds of the invention are thus very useful as antitumor agents for treating cancers in man and animals. Particularly the compounds of the invention have excellent properties including (1) high solubility in water, (2) good absorption, (3) long-lasting effect, (4) high stability, (5) significantly low gastrointestinal toxicity, hence freedom from diarrhea, vomiting and gastrointestinal bleeding, and (6) great difference between the effective dose for producing the desired anticancer effect and the dose inducing side effects such as those due to toxicity, hence excellent in therapeutic index, safety, etc. Therefore the compounds of the invention can be administered to the patient in such dosage forms as injection solution, orally administrable preparations, suppositories and the like to achieve excellent pharmacological effect.

The desired products of the present invention are used in the form of generally acceptable pharmaceutical compositions which are prepared by using diluents or excipients such as fillers, bulking agents, binders, wetting agents, disintegrating agents, surfactants, lubricnats and the like. Administration unit forms of these pharmaceutical compositions of the present invention can be varied and selected so as to meet various therapeutical purposes. Typical forms of the pharmaceutical compositions include tablets, pills, powders, liquids, suspensions, emulsions, granules, capsules, suppositories, injections (liquids, suspensions and others), ointments and the like.

In shaping into the form of tablets, those known as the carriers in this field can widely be applied for example, excipients such as lactose, purified sugar, sodium chloride, glucose, urea, starch, calcium carbonate, kaolin, crystalline cellulose, silicic acid and others; binders such as water, ethanol, propanol, simple syrup, glucose solution, starch solution, gelatin solution, carboxymethyl cellulose, shellac, methyl cellulose, potassium phosphate, polyvinylpyrrolidone and others; disintegrating agents such as dried starch, sodium alginate, powdered agar, laminaran powder, sodium hydrogen carbonate, calcium carbonate, a fatty acid ester of polyoxyethylene sorbitan, sodium laurylsulfate, monoglyceride of stearic acid, starch, lactose and others; disintegration inhibitors such as purified sugar, stearin, cacao butter, hydrogenated oils and others; absorbefacients such as quaternary ammonium base, sodium laurylsulfate and others; wetting agents such as glycerin, starch and others; adsorbents such as starch, lactose, kaolin, bentonite, colloidal silicic acid and others; and lubricants such as purified talc, stearic acid salts, boric acid powder, polyethylene glycol and others can be exemplified. If necessary, the tablets can further be coated with usual coating, for example sugar coated tablets, gelatin film-coated tablets, enteric coated tablets, film-coated tablets, or double-layered tablets, multiple-layered tablets and others. In shaping into the form of pills, those known as the carriers in this field can widely be applied for example, excipients such as glucose, lactose, starch, cacao butter, hardened vegetable oils, kaolin, talc and others; binders such as powdered gum arabi, powdered traganth, gelatin, ethanol and others; disintegrating agent such as laminaran, agar and others. In shaping into the form of suppositories, carriers known in this field can widely be applied for example, polyethylene glycol, cacao butter, a higher alcohol, an ester of a higher alcohol, gelatin, semi-synthesized glyceride and others. Capsules are prepared in a conventional manner by admixing the compound of the invention with the foregoing various carrier and encapsulating the mixture into hard-gelatin capsules, soft-gelatin capsules, etc. In case of preparing injections, solutions, emulsions and suspensions being prepared are sterilized, and they are preferably isotonic to the blood. In preparing into the form of solutions, emulsions and suspensions, those known as the diluents in this field can widely be applied, for example water, ethanol, macrogol, propylene glycol, ethoxylated isostearyl alcohol, polyoxylated isostearyl alcohol, polyoxyethylene sorbitan fatty acid ester and others. In case of preparing isotonic solutions, sufficient amount of sodium chloride, glucose or glycerin may be added to make the solution to be isotonic to the blood. The pharmaceutical compositions for injection preparation may further be contain usual solubilizers, buffer solutions, soothing agents or the like if necessary. In shaping into the form of pastes, creams and gels, diluents such as white vaseline, paraffins, glycerine, cellulose derivatives, polyethylene glycols, silicones, bentonite and the like can be used.

The pharmaceutical composition of the present invention may also contain coloring agents, preservatives, perfumes, seasoning agents, sweetening agents and others, as well as contain other medicines, if necessary.

The amount of the compound according to the present invention to be contained as the active ingredient in the pharmaceutical composition is not specifically restricted and can be selected from a wide range, generally 1 to 70 % by weight, may be used.

Administration method of the above-mentioned pharmaceutical composition is not specifically restricted and can be administered through a suitable method for the respective types of administration forms, depending upon age, sex, other conditions, and the symptons of the patient and others. For example, tablets, pills, liquids, suspensions, emulsions, granules and capsules are administered orally; injections are administered intravenously singly or as a mixture with usual injectable transfusions such as a glucose solution and an amino acids solutions; and if necessary the injections are administered singly intramuscularly, intracutaneously, subcutaneously or intraperitoneally; and the suppositories are administered into rectum.

The dosage of the desired products of the present invention may suitably be selected depending upon the method for administration, age, sex and other conditions, and conditions of the symptoms of the patients, and generally the pharmaceutical compositions of the invention can be administered in an amount of about 0.5 to about 20 mg/kg of the body weight/day, calculated as the compound of the invention (active ingredient), in a single dose or in 2 to 4 divided doses.

The present invention will be described in greater detail with reference to the following reference examples, examples, pharmaceutical tests and preparation examples.

In connection with the NMR data in the reference examples and examples, the numerals used as a subscript at the right of the symbol "C" or "N" are used to refer to the position in the compound. Thus the term "$C_6$-H", for example, refers to the hydrogen bonded to the carbon atom at the 6-position. Similarly the term "$C_{3',4',5'}$—H", for example, denotes the hydrogens bonded to the carbon atoms at the 3'-, 4'- and 5'-positions.

Reference Example 1

Preparation of 2'-deoxy-5-fluoro-3'-O-furfuryluridine

To a solution of 1.00 g of 2'-deoxy-5-fluoro-5'-O-trityluridine in 30 ml cf dioxane were added 0.35 g of finely divided powder of potassium hydroxide and 0.29 g of furfuryl chloride, and the mixture was stirred at 80° C. for 2 hours. The solvent was evaporated off and the residue was dissolved in 30 ml of ethyl acetate The solution was washed with water, dried and concentrated. The residue was dissolved in 15 ml of 80% acetic acid and the solution was left to stand at 80° C. for 2 hours The solvent was evaporated off and the residue was dissolved in 30 ml of ethyl acetate, and the solution was washed with water, dried and concentrated. The residue was treated with chloroform and the insoluble matters were filtered and recrystallized from ethanol, thereby giving 0.37 g of 2'- deoxy-5 fluoro-3'-O-furfuryluridine.

Yield: 55%
Melting point: 186°–188° C.
NMR (DMSO-$d_6$) δ
11.82 (1H, bs, NH), 8.19 (1H, d, J=6Hz, $C_6$-H),
7.65-7.63 (1H, m, $C_5$-H of the furan ring)
6.60-6.40 (2H, m, $C_{3,4}$-H of the furan ring),
6.09 (1H, t, J=7Hz, $C_{1'}$-H), 5.22 (1H, bs, $C_{5'}$-OH)
4.49 (2H, s,

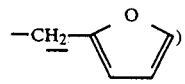

4.21-4.12 (1H, m, $C_{3'}$-H), 4.01-3.92 (1H, m, $C_{4'}$-H),
3.64-3.55 (2H, m, $C_{5'}$-H), 2.25-2.11 (2H, m, $C_{2'}$-H)

Reference Examples 2–13

Following the general procedure of Reference Example 1 and using appropriate starting materials, the compounds having the following structural formula and shown in Table 1A below were prepared

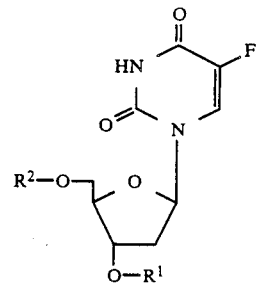

Table 1A below shows the structure, yields and melting points or form of the products thus obtained, and Table 1B below shows NMR spectral data thereof.

TABLE 1A

| Ref. Ex No. | $R^1$ | $R^2$ | Yield (%) | M.p. (°C.) or Form |
|---|---|---|---|---|
| 2 | -CH2-furan(O) | H | 37 | 167–168 |
| 3 | -CH2-thiophene(S) | H | 54 | Powder |
| 4 | -CH2-thiophene(S) | H | 40 | 183–184 |
| 5 | -CH2-thiophene(S)-Cl | H | 62 | 133–134 |
| 6 | -CH2-thiophene(S)-Br | H | 35 | Powder |
| 7 | -CH2-thiophene(S)-Br, Br | H | 39 | 110–112 |
| 8 | -CH2-thiophene(S)-Cl, Cl | H | 74 | 147–149 |
| 9 | -CH2-thiophene(S)-Cl | H | 40 | Powder |

TABLE 1A-continued

| Ref. Ex No. | R¹ | R² | Yield (%) | M.p. (°C.) or Form |
|---|---|---|---|---|
| 10 | —CH₂—(thiophene, Br) | H | 55 | Powder |
| 11 | —CH₂—(thiophene, C₂H₅) | H | 20 | Powder |
| 12 | H | —CH₂—(thiophene, Cl) | 51 | Powder |
| 13 | —CH₂—(thiophene, Br, Br) | H | 7 | Powder |

TABLE 1B

| Ref. Ex No. | NMR (DMSO-$d_6$): δ |
|---|---|
| 2 | 11.80 (1H, bs, NH)<br>8.18 (1H, d, J = 7 Hz, $C_6$—H)<br>7.64–7.60 (2H, m, $C_{2,5}$—H of the furan ring)<br>6.50–6.47 (1H, m, $C_4$—H of the furan ring)<br>6.09 (1H, t, J = 7 Hz, $C_1'$—H)<br>5.17 (1H, t, J = 5 Hz, $C_5'$—OH)<br>4.40 (2H, s, —CH₂—)<br>4.22–4.10 (1H, m, $C_3'$—H)<br>4.04–3.94 (1H, m, $C_4'$—H)<br>3.64–3.57 (2H, m, $C_5'$—H)<br>2.29–2.12 (2H, m, $C_2'$—H) |
| 3 | 11.79 (1H, bs, NH)<br>8.18 (1H, d, J = 7 Hz, $C_6$—H)<br>7.56–7.43 (2H, m, $C_{2,5}$—H of the thiophene ring) 7.09 (1H, dd, J = 1 Hz, J = 5 Hz, $C_4$—H of the thiophene ring)<br>6.19–6.02 (1H, m, $C_1'$—H)<br>5.17 (1H, t, J = 4 Hz, $C_5'$—OH)<br>4.53 (2H, s, —CH₂—)<br>4.20–4.14 (1H, m, $C_3'$—H)<br>4.02–3.99 (1H, m, $C_4'$—H)<br>3.64–3.60 (2H, m, $C_5'$—H)<br>2.29–2.12 (2H, m, $C_2'$—H) |
| 4 | 11.80 (1H, d, NH)<br>8.18 (1H, d, J = 7 Hz, $C_6$—H)<br>7.50 (1H, dd, J = 1 Hz, J = 5 Hz, $C_5$—H of the thiophene ring)<br>7.17–6.95 (2H, m, $C_{3,4}$—H of the thiophene ring)<br>6.19–6.05 (1H, m, $C_1'$—H)<br>5.18 (1H, t, J = 5 Hz, $C_5'$—OH)<br>4.71 (2H, s, —CH₂—)<br>4.26–4.14 (1H, m, $C_3'$—H)<br>4.05–3.95 (1H, m, $C_4'$—H)<br>3.63–3.56 (2H, m, $C_5'$—H)<br>2.34–1.96 (2H, m, $C_2'$—H) |
| 5 | solvent: CDCl₃<br>9.64 (1H, bs, NH)<br>7.95 (1H, d, J = 6 Hz, $C_6$—H)<br>6.76 (2H, s, $C_{3,4}$—H of the thiophene ring)<br>6.20 (1H, t, J = 6 Hz, $C_1'$—H)<br>4.59 (2H, s, —CH₂—)<br>4.32–4.19 (1H, m, $C_3'$—H)<br>4.14–4.05 (1H, m, $C_4'$—H)<br>4.00–3.66 (2H, m, $C_5'$—H)<br>2.98 (1H, bs, $C_5'$—OH)<br>2.59–1.99 (2H, m, $C_2'$—H) |
| 6 | 11.80 (1H, bs, NH)<br>8.19 (1H, d, J = 7 Hz, $C_6$—H)<br>7.10 and 6.93 (each 1H, d, J = 4 Hz, $C_3$—H or $C_4$—H of the thiophene ring)<br>6.11 (1H, t, J = 6 Hz, $C_1'$—H)<br>5.20 (1H, bs, $C_5'$—OH)<br>4.67 (2H, s, —CH₂—)<br>4.24–4.16 (1H, m, $C_3'$—H)<br>4.06–3.99 (1H, m, $C_4'$—H)<br>3.77–3.47 (2H, m, $C_5'$—H)<br>2.40–2.07 (2H, m, $C_2'$—H) |
| 7 | 11.81 (1H, bs, NH)<br>8.19 (1H, d, J = 7 Hz, $C_6$—H)<br>7.28 (1H, s, H of the thiophene ring)<br>6.11 (1H, t, J = 6 Hz, $C_1'$—H)<br>5.21 (1H, t, J = 5 Hz, $C_5'$—OH)<br>4.63 (2H, s, —CH₂—)<br>4.24–4.19 (1H, m, $C_3'$—H)<br>4.09–3.98 (1H, m, $C_4'$—H)<br>3.67–3.58 (2H, m, $C_5'$—H)<br>2.33–2.16 (2H, m, $C_2'$—H) |
| 8 | 11.81 (1H, bs, NH)<br>8.17 (1H, d, J = 7 Hz, $C_6$—H)<br>7.12 (1H, s, H of the thiophene ring)<br>6.09 (1H, t, J = 6 Hz, $C_1'$—H)<br>5.19 (1H, t, J = 5 Hz, $C_5'$—OH)<br>4.66 (2H, s, —CH₂—)<br>4.25–4.16 (1H, m, $C_3'$—H)<br>4.05–3.95 (1H, m, $C_4'$—H)<br>3.65–3.56 (2H, m, $C_5'$—H)<br>2.44–2.37 (2H, m, $C_2'$—H) |
| 9 | 11.81 (1H, bs, NH)<br>8.17 (1H, d, J = 6 Hz, $C_6$—H)<br>7.66 (1H, d, J = 5 Hz, $C_5$—H of the thiophene ring)<br>7.06 (1H, d, J = 5 Hz, $C_4$—H of the thiophene ring)<br>6.12 (1H, t, J = 6 Hz, $C_1'$—H)<br>5.21 (1H, t, J = 5 Hz, $C_5'$—OH)<br>4.68 (2H, s, —CH₂—)<br>4.30–4.17 (1H, m, $C_3'$—H)<br>4.05–3.96 (1H, m, $C_4'$—H)<br>3.67–3.58 (2H, m, $C_5'$—H)<br>2.38–2.16 (2H, m, $C_2'$—H) |
| 10 | 11.81 (1H, bs, NH)<br>8.20 (1H, d, J = 7 Hz, $C_6$—H)<br>7.65 (1H, d, J = 5 Hz, $C_5$—H of the thiophene ring) |

4,992,534

TABLE 1B-continued

| Ref. Ex No. | NMR (DMSO-d$_6$): δ |
|---|---|
| | 7.09 (1H, d, J = Hz, C$_4$—H of the thiophene ring) |
| | 6.13 (1H, t, J = 7 Hz, C$_1'$—H) |
| | 5.21 (1H, bs, C$_5'$—OH) |
| | 4.67 (2H, s, —CH$_2$—) |
| | 4.28–4.20 (1H, m, C$_3'$—H) |
| | 4.08–4.00 (1H, m, C$_4'$—H) |
| | 3.64 (2H, bs, C$_5'$—H) |
| | 2.40–2.17 (2H, m, C$_2'$—H) |
| 11 | 11.80 (1H, bs, NH) |
| | 8.18 (1H, d, J = 7 Hz, C$_6$—H) |
| | 6.86 and 6.69 (each, 1H, d, J = 4 Hz, C$_3$—H or C$_4$—H of the thiophene ring) |
| | 6.18–6.01 (1H, m, C$_1'$—H) |
| | 5.17 (1H, t, J = 5 Hz, C$_5'$—OH) |
| | 4.62 (2H, s, —CH$_2$—) |
| | 4.24–4.13 (1H, m, C$_3'$—H) |
| | 4.04–3.97 (1H, m, C$_4'$—H) |
| | 3.64–3.55 (2H, m, C$_5'$—H) |
| | 2.78 (2H, q, J = 7 Hz, CH$_2$CH$_3$) |
| | 2.25–2.02 (2H, m, C$_2'$—H) |
| | 1.22 (3H, t, J = 7 Hz, CH$_3$) |
| 12 | 11.79 (1H, bs, NH) |
| | 7.89 (1H, d, J = 7 Hz, C$_6$—H) |
| | 7.01 and 6.94 (each, 1H, d, J = 4 Hz, C$_3$—H or C$_4$—H of the thiophene ring) |
| | 6.12 (1H, td, J = 7 Hz, J = 2 Hz, C$_1'$—H) |
| | 5.31 (1H, d, J = 4 Hz, C$_3'$—OH) |
| | 4.65 (2H, s, —CH$_2$—) |
| | 4.26–4.08 (1H, m, C$_3'$—H) |
| | 3.90–3.74 (1H, m, C$_4'$—H) |
| | 3.68–3.61 (2H, m, C$_5'$—H) |
| | 2.18–2.05 (2H, m, C$_2'$—H) |
| 13 | solvent: CDCl$_3$ |
| | 8.96 (1H, bs, NH) |
| | 7.92 (1H, d, J = 6 Hz, C$_6$—H) |
| | 6.82 (1H, s, C$_3$—H of the thiophene ring) |
| | 6.27–6.09 (1H, m, C$_1'$—H) |
| | 4.60 (2H, s, —CH$_2$—) |
| | 4.31–4.19 (1H, m, C$_3'$—H) |
| | 4.13–4.07 (1H, m, C$_4'$—H) |
| | 3.89–3.78 (2H, m, C$_5'$—H) |
| | 2.63 (1H, bs, C$_5'$—OH) |
| | 2.39–1.96 (2H, m, C$_2'$—H) |

EXAMPLE 1

Preparation of 5'-O-[N-(t-butoxycarbonyl)glycyl]-3'-O-(5-chloro-2-thenyl)-2'-deoxy-5-fluorouridine and 3'-O-(5-chloro-2-thenyl)-2'-deoxy-5-fluoro-5'-O-glycyluridine hydrochloride To a solution of 11.70 g of N-(t-butoxycarbonyl)glycine in 200 ml of acetonitrile were added 8.27 g of 1,3-dicyclohexylcarbodiimide, and the mixture was stirred with ice-cooling for 3 hours.

The reaction mixture was concentrated under reduced pressure and the anhydride thus formed was dissolved in 200 ml of pyridine and 6.28 g of 3'-O-(5-chloro-2-thenyl)-2'-deoxy-5-fluorouridine was added thereto, followed by reaction at room temperature for 3 days. The solvent was evaporated off and the residue was distributed between ethyl acetate and water. The organic layer was washed with a saturated aqueous solution of sodium hydrogencarbonate, dried over anhydrous magnesium sulfate and concentrated. The residue was placed on silica gel column and eluted with chloroform for purification, giving 7.24 g of 5'-O-[N-(t-butoxycarbonyl)glycyl]-3'-O-(5-chloro-2-thenyl)-2'-deoxy-5-fluorouridine.

Elemental analysis for C$_{21}$H$_{25}$ClFN$_3$O$_8$S·H$_2$O
Calcd.: C., 45.70%; H, 4.93%; N, 7.61%.
Found : C., 46.01%; H, 5.13%; N, 7.68%.
NMR (DMSO-d$_6$) δ:
11.85 (1H, bs, N$_3$-H), 7.92 (1H, d, J=7Hz, C$_6$-H),
7.20 (1H, t, J=6Hz, CONH),
6.99 (2H, bs,

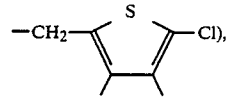

6.18–6 03 (1H, m, C$_1'$-H)
4.66 (2H, s,

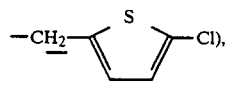

4.24–4.14 (4H, m, C$_{3',4',5'}$-H),
3.71 (2H, d, J=6Hz, COCH$_2$),
2.34–2.22 (2H, m, C$_2'$-H), 1.34 (9H, s, CH$_3$ ×3).

Then, the product thus obtained was dissolved in 20 ml of 4N hydrochloric acid-dioxane and the solution was stirred at room temperature for 1 hour.

The reaction mixture was concentrated under reduced pressure, and the residue was placed on silica gel column and eluted with 8% methanol-chloroform for purification, giving 3.77 g of 3'-O-(5-chloro-2-thenyl) 2'-deoxy-5-fluoro-5'-O-glycyluridine hydrochloride.

Yield 48%.
Form : Hygroscopic powder.
Elemental analysis for C$_{16}$H$_{17}$ClFN$_3$O$_6$S·HCl·5/2 H$_2$O.
Calcd.: C., 37.29%; H, 4.50%; N, 8.15%.
Found : C., 37.37%; H, 4.68%; N, 8.06%.
NMR (DMSO-d$_6$) δ:
9.27 (3H, bs, NH$_2$. HCl), 8.01 (1H, d, J=7Hz, C$_6$-H),
7.00 (2H, s,

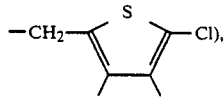

6.18–6.04 (1H C$_1'$-H)
4.68 (2H, s,

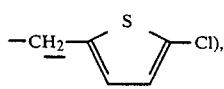

4.38–4.05 (4H, m, C$_{3'4',5'}$-H),
3.81 (2H, s, CH$_2$CO), 2.47–2.26 (2H, m, C$_2'$-H)

EXAMPLE 2

Following the general procedure of Example 1 and using appropriate starting materials, the compound of the following structural formula and shown in Table 2 below was prepared.

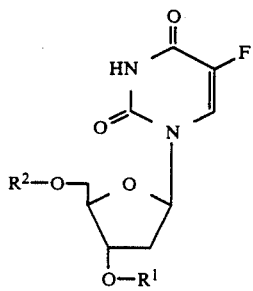

(1)

Table 2 below shows the structure, yield, form and NMR spectral data of the product thus obtained.

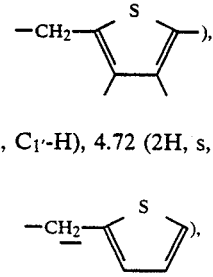

6.20-6.03 (1H, m, C$_{1'}$-H), 4.72 (2H, s, 4.23-4.14 (4H, m, C$_{3', 4', 5'}$-H),
3.71 (2H, d, J=6Hz, COCH$_2$),

TABLE 2

| Ex. No. | R$^1$ | R$^2$ | Yield (%) | Form | NMR (DMSO-d$_6$): δ |
|---|---|---|---|---|---|
| 2 | —CH$_2$-furan | HCl·NH$_2$CH$_2$C(=O)— | 5 | Hygroscopic powder | 11.86 (1H, bs, NH) 9.01 (3H, bs, NH$_2$, HCl) 8.01 (1H, d, J=7Hz, C$_6$—H) 7.66 (1H, s, —CH$_2$-furan) 6.50-6.41 (2H, m, —CH$_2$-furan) 6.09 (1H, t, J=6Hz, C$_1'$—H) 4.52 (2H, s, —CH$_2$-furan) 4.37-4.08 (4H, m, C$_{3',4',5'}$—H) 3.81 (2H, s, CH$_2$CO) 2.38-2.22 (2H, m, C$_2'$—H) |

EXAMPLE 3

Preparation of 5'-O-[N-(t-butoxycarbonyl)glycyl]-2'-deoxy-5-fluoro-3'-O-(2-thenyl)uridine and 2'-deoxy-5-fluoro-5'-O-glycyl-3'-O-(2-thenyl)-uridine hydrochloride Following the general procedure of Example 1 and using appropriate starting materials, there was obtained 1.04 g of 5'-O-[N-(t-butoxycarbonyl)glycyl]-2'-deoxy-5-fluoro-3'-O-(2-thenyl)uridine.

Elemental analysis: for C$_{21}$H$_{26}$FN$_3$O$_8$S·1/2H$_2$O:
Calcd.: C., 49.60%; H, 5.35%; N, 8.26%.
Found : C, 49.67%; H, 5.66%; N, 8.16%.
NMR (DMSO-d$_6$) δ:
11.84 (1H, bs, N$_3$-H), 7.92 (1H, d, J=7Hz, C$_6$-H),
7.55- 7.48 (1H, m,

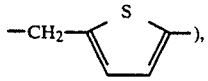

7.28-6.96 (3H, m, NH, 2.34-2.21 (2H, m, C$_{2'}$-H), 1.37 (9H, s, CH$_3$ ×3):

The above product was dissolved in 50 ml of anhydrous acetonitrile, and after replacing the atmosphere within the reaction system with nitrogen gas, 0.65 ml of iodotrimethylsilane was added thereto with ice-cooling and the reaction was effected for 10 minutes. Then 0.34 ml of methanol was added thereto and the mixture was left to stand for 1 hour, followed by addition of 2.08 ml of 1N hydrochloric acid.

The reaction mixture was concentrated under reduced pressure and the residue was placed on silica gel column and eluted with 8% methanol-chloroform for purification, giving (0.21 g of 2'-deoxy-5-fluoro-5'-O-glycyl-3'-O-(2-thenyl)uridine hydrochloride.
Yield: 23%:
Form : Hygroscopic powder.
Elemental analysis: for C$_{16}$H$_{18}$FN$_3$O$_6$S·HCl·H$_2$O:
Calcd.: C, 42.341%; H, 4.66%; N, 9.26%.
Found: C, 42.04%; H, 5.01%; N, 9.43%.
NMR (DMSO-hd6) δ:
11.50 (1H, bs, NH), 8.30 (3H, bs, NH$_2$, HCl),
7.97 (1H, d, J=7Hz, C$_6$-H),
7.52 (1H, dd, J=1Hz, J=5Hz,

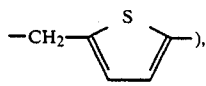

7.09-6.97 (2H, m,

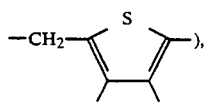

6.25 6.07 (1H, m, C$_{1'}$-H), 4.74 (2H, s,

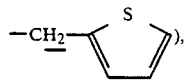

4.39 4.11 (4H, m, C$_{3', 4', 5'}$-H), 3.84 (2H, s, CH$_2$CO), 2.39-2.26 (2H, m, C$_{2'}$-H).

EXAMPLE 4

Preparation of 3'-O-(5-bromo-2-thenyl)-5'-O-[N-(t-butoxycarbonyl)-glycyl]-2'-deoxy-5-fluorouridine and 3'-O-(5-bromo-2-thenyl)-2'-deoxy-5-fluoro-5'-flycyluridine hydrochloride To a solution of 1.00 g of 3'-O-(5-bromo-2-thenyl)-2'-deoxy-5-fluorouridine in 30 ml of pyridine were added 0.62 g of N-(t-tutoxycarbonyl)glycine and 1.44 g of triisopropylbenzenesulfonyl chloride, and the mixture was stirred at room temperature for 48 hours.

The reaction mixture was concentrated under reduced pressure and the residue was distributed between ethyl acetate and a saturated aqueous solution of sodium hydrogencarbonate. The organic layer was washed with 1N hydrochloric acid and a saturated aqueous solution of sodium chloride, dried over anhydrous sodium sulfate and concentrated. The residue was placed on silica gel column and eluted with 1% methanol-chloroform for purification, giving 1.33 g of 3'-O-(5-bromo-2-thenyl)-5'-O-[N-(t-butoxycarbonyl)glycyl]-2'-deoxy-5-fluorouridine.

Elemental analysis: for C$_{21}$H$_{25}$BrFN$_3$O$_8$S:
Calcd.: C, 43.61%; H, 4.36%; N, 7.26%.
Found : C, 43.37%; H, 4.72%; N, 7.06%.
NMR (DMSO-d$_6$) δ:
11.85 (1H, bd, N$_3$-H), 7.92 (1H, d, J=7Hz, C$_6$-H), 7.27-7.09 (2H, m, CONH

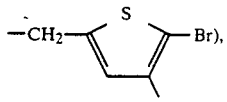

6.94 (1H, d, J=4Hz,

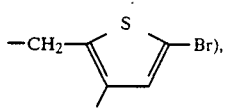

6.11 (1H, t, J=6Hz, C$_{1'}$-H),
4.67 (2H, s,

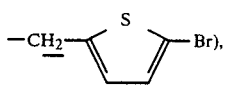

4.33-4.14 (4H, m, C$_{3', 4', 5'}$-H),
3.71 (2H, d, J=6Hz, COCH$_2$), 2.34-2.22 (2H, m, C$_{2'}$-H), 1.37 (9H, s, CH$_3$ ×3).

Then, to the product thus obtained was added 5 ml of 4N hydrochloric acid-dioxane and the mixture was left to stand at room temperature for 15 minutes. The reaction mixture was concentrated and to the residue thus formed was added 50 ml of ether. The precipitate thus formed was filtered and placed on silica gel column and eluted with 4%-7% methanol-chloroform for purification, giving 0.73 g of 3'-O-(5-bromo-2thenyl)-2'-deoxy-5fluoro-5'-O-glycyluridine hydrochloride.

Yield: 58%:
Form: Hygroscopic powder.
Elemental analysis: for C$_{16}$H$_{17}$BrFN$_3$O$_6$S·HCl·3/2 H$_2$O:
Calcd.: C, 35.47%; H, 3.91%; N, 7.76%.
Found : C, 35.64%; H, 4.06%; N, 7.66%.
NMR (DMSO-d$_6$) δ:
11.70 (1H, bs, NH), 9.15 (3H, bs, NH$_2$, HCl),
8.01 (1H, d, J=7Hzz, C$_6$-H),
7.12 (1H, d, J=4Hz,

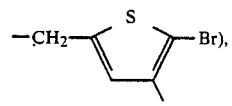

6.90 (1H, d, J=4Hz,

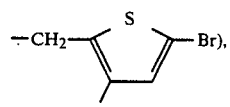

6.11 (1H, t, J=6Hz, C$_{1'}$-H),
4.70 (2H, s,

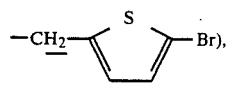

4.39-4.06 (4H, m, C$_{3', 4', 5'}$-H),
3.81 (2H, s, CH$_2$CO), 2.49-2.26 (2H, m, C$_{2'}$-H).

EXAMPLE 5

Preparation of 5'-O-(3-carboxypropanoyl)-2'-deoxy-5-fluoro-3'-O-(2-thenyl)uridine To a solution of 1.24 g of 2'-deoxy-5-fluoro-3'-O-(2-thenyl)uridine in 30 ml of pyridine was added 1.06 g of succinic anhydride, and the mixture was stirred overnight at 80° C.

The reaction mixture was concentrated under reduced pressure and the residue was distributed between chloroform and water The organic layer was dried over anhydrous magnesium sulfate and concentrated again under reduced pressure The residue was placed on silica gel column and eluted with 2% methanol-chloroform for purification, giving 1.44 g of 5'-O-(3-carboxypropanoyl) 2'-deoxy-5-fluoro-3'-O-(2-thenyl)uridine.

Yield: 90%.
Form : Powder.
Elemental analysis: for C$_{18}$H$_{19}$FN$_2$O$_8$S·1/2H$_2$O.
Calcd.: C., 47.89%; H, 4.47%; N, 6.21%.
Found : C., 47.89%; H, 4.69%; N, 5.96%.
NMR (DMSO-d$_6$) δ:
12.16 (1H, bs, COOH), 11.86 (1H, bs, NH)
7.92 (1H, d, J=7Hz, C$_6$-H), 7.51 (1H, dd, J=2Hz, J=5Hz,

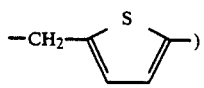

7.11-6.96 (2H, m,

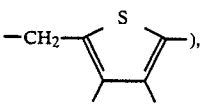

6.17-6.02 (1H, m, $C_{1'}$-H), 4.72 (2H, s,

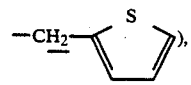

4.20 (4H, bs, $C_{3', 4', 5'}$-H),
2.52 (4H, s, —COCH$_2$CH$_2$CO—), 2.35-2.23 (2H, m, $C_{2'}$-H).

EXAMPLE 6

Following the general procedure of Example 5 and using appropriate starting materials, the compound having the following structural formula and shown in Table 3 below was obtained.

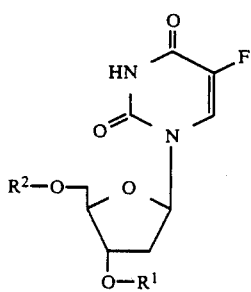

Table 3 below shows the structure, yield, form and NMR spectral data of the product thus obtained.

EXAMPLE 7

Preparation of 5'-O-[N-(t-butoxycarbonyl)-β-alanyl]-3'-O-(5-chloro-2-thenyl)-2'-deoxy-5-fluorouridine To a solution of 2.01 g of N-(t-butoxycarbonyl)β-alanine in 50 ml of acetonitrile was added 1.31 g of 1,3-dicyclohexylcarbodiimide, and the mixture was stirred with ice-cooling for 2 hours.

The reaction mixture was filtered and concentrated. To the residue were added 50 ml of pyridine and 1.00 g of 3'-O-(5-chloro-2-thenyl)-2'-deoxy-5-fluorouridine, and the mixture was subjected to reaction at room temperature overnight The solvent was evaporated off and the residue was dissolved in 30 ml of ethyl acetate. The solution was washed with water, dried and concentrated. The residue was placed on silica gel column and eluted with chloroform for purification, thereby giving 0.85 g of the desired 5'-O-[N-(t-butoxycarbonyl)-β-alanyl]-3'-O-(5-chloro-2-thenyl)-2'-deoxy-5-flurouridine.

Yield: 59%.

Form : Hygroscopic powder.

Elemental analysis: for $C_{22}H_{27}ClFN_3O_8S \cdot H_2O$:

Calcd.: C., 46.69%; H, 5.16%; N, 7.42%

Found : C., 46.69%; H, 5.28%; N, 7.60%

NMR (DMSO-$d_6$) δ:

11.83 (1H, bs, $N_3$-H), 7.92 (1H, d, J=7Hz, $C_6$-H), 7.03-6.94 (2H, m,

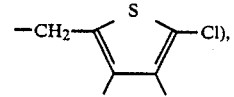

6.79 (1H, bs, NH), 6.20-6.01 (1H, m, $C_{1'}$-H), 4.66 (2H, s,

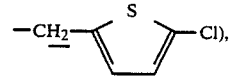

4.19 (4H, bs, $C_{3',4', 5'}$-H), 3.28-3.06 (2H, m, NHCH$_2$), 2.57-2.24 (m, coalesced with DMSO, $C_{2'}$-H and

TABLE 3

| Ex. No. | R$^1$ | R$^2$ | Yield (%) | Form | NMR (DMSO-$d_6$): δ |
|---|---|---|---|---|---|
| 6 | —CH$_2$—⟨thienyl⟩—Cl | —CO(CH$_2$)$_2$COOH | 78 | Powder | 12.18 (1H, bs, COOH)<br>11.85 (1H, d, NH)<br>7.91 (1H, d, J=7Hz, $C_6$—H)<br>6.99 (2H, s, —CH$_2$—⟨thienyl⟩—Cl)<br>6.21-6.05 (1H, m, $C_1'$—H)<br>4.65 (2H, s, —CH$_2$—⟨thienyl⟩—Cl)<br>4.21 (4H, bs, $C_{3',4',5'}$—H)<br>2.52 (4H, s, —COCH$_2$CH$_2$CO—)<br>2.35-2.24 (2H, m, $C_2'$—H) |

COCH$_2$), 1.36 (9H, s, CH$_3$ ×3).

EXAMPLE 8

Preparation of 3'-O-(N-benzyloxycarbonylglycyl)-2'-deoxy 5-fluoro-5'-O-furfuryluridine To a solution of 2.56 g of N-benzyloxycarbonylglycine glycine in 50ml of acetonitrile was added 1.52 g of 1,3-dicyclohexylcarbodiimide, and the mixture was stirred with ice-cooling for 2 hours.

The reaction mixture was filtered and concentrated. To the residue were added 50 ml of pyridine and 1.00 g of 2'-deoxy-5-fluoro-5'-O-furfuryluridine, and the mixture was subjected to reaction at room temperature for 1 day. The solvent was evaporated off and the residue was dissolved in 30 ml of ethyl acetate The solution was washed with a saturated aqueous solution of sodium hydrogen carbonate, dried and concentrated. The resulting residue was placed on silica gel column and eluted with 1% methanol-chloroform for purification, thereby giving 1.20 g of 3'-O-(N-benzyloxycarbonylglycyl)-2'-deoxy-5- fluoro-5'-O-furfuryluridine.

Yield: 76%.
Form : Powder.
Elemental analysis: for $C_{24}H_{24}FN_3O_9$:
Calcd.: C., 55.71%; H, 4.68%; N, 8.12%.
Found : C., 55.83%; H, 4.97%; N, 8.35%.

EXAMPLE 9

Preparation of 3'-O-[N-(t-butoxycarbonyl)glycyl]-2'-deoxy-5-fluoro-5'-O-(2-thenyl)uridine To a solution of 2.05 g of N-(t-butoxycarbonyl)glycine in 50 ml of acetonitrile was added 1.45 g of 1,3-dicyclohexylcarbodiimide, and the mixture was stirred with ice-cooling for 3 hours.

The reaction mixture was filtered and concentrated. To the residue were added 50 ml of pyridine and 1.00 g of 2'-deoxy-5-fluoro-5'-O-(2-thenyl)uridine, and the mixture was subjected to reaction at room temperature for 1 day. The solvent was evaporated off and the residue was dissolved in 30 ml of ethyl acetate. The solution was washed with water, dried and concentrated. The resulting residue was placed on silica gel column and eluted with 1% methanol-chloroform for purification, thereby giving 1.17 g of 3'-O-[N-(t-butoxycarbonyl)-glycyl]-2'-deoxy-5-fluro-5'-O-(2-thenyl)uridine.

Yield: 80%.
Form : Hygroscopiec powder.
Elemental analysis: for $C_{21}H_{26}FN_3O_8S \cdot H_2O$:
Calcd.: C., 48.74%; H, 5.45%; N, 8.12%.
Found : C., 48.85%; H, 5.21%; N, 7.93%.

EXAMPLES 10–18

Following the general procedure of Example 7 and using appropriate starting materials, the compounds having the following structural formula and shown in Table 4 below were prepared

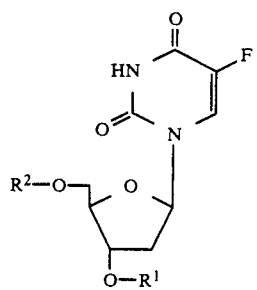

TABLE 4

| Ex. No. | R¹ | R² | Yield (%) | Form | NMR (DMSO-d$_6$): δ |
|---|---|---|---|---|---|
| 10 | -CH$_2$-[5-chlorothiophene] | -C(=O)-CH(NHCOC(CH$_3$)$_3$)CH(CH$_3$)$_2$ (L) | 98 | Hygroscopic powder | 11.86 (1H, d, N$_3$—H) 7.89 (1H, d, J=7Hz, C$_6$—H) 7.23–6.93 (3H, m, NH, —CH$_2$-[5-chlorothiophene]) 6.21–6.03 (1H, m, C$_1'$—H) 4.66 (2H, s, —CH$_2$—) 4.30–4.19 (4H, m, C$_3'$,4',5'—H) 3.91–3.74 (1H, m, COCH) 2.37–2.24 (2H, m, C$_2'$—H) 2.08–1.92 (1H, m, CH(CH$_3$)$_2$) 1.36 (9H, s, C(CH$_3$)$_3$) 0.87 (6H, d, J=7Hz, CH(CH$_3$)$_2$) |
| 11 | -CH$_2$-[5-chlorothiophene] | -C(=O)-CH(NHCOC(CH$_3$)$_3$)(CH$_2$)$_2$SCH$_3$ (L) | 89 | Hygroscopic powder | 11.86 (1H, bs, N$_3$—H) 7.88 (1H, d, J=7Hz, C$_6$—H) 7.34 (1H, d, J=7Hz, NH) 7.03–6.93 (2H, m, —CH$_2$-[5-chlorothiophene]) 6.21–6.06 (1H, m, C$_1'$—H) 4.66 (2H, s, —CH$_2$—) 4.23–4.06 (5H, m, C$_3'$,4',5'—H, COCH) 2.54–2.23 (m coalesced with DMSO, C$_2'$—H, CHCH$_2$) 2.04–1.74 (5H, m, CH$_2$SCH$_3$) 1.35 (9H, s, C(CH$_3$)$_3$) |
| 12 | -CH$_2$-[5-chlorothiophene] | -C(=O)-CHCH$_3$(NHCOC(CH$_3$)$_3$) (D) | 85 | Hygroscopic powder | 11.82 (1H, bs, N$_3$—H) 7.91 (1H, d, J=7Hz, C$_6$—H) 7.28 (1H, bd, NH) 7.02–6.92 (2H, m, —CH$_2$-[5-chlorothiophene]) 6.18–5.99 (1H, m, C$_1'$—H) 4.66 (2H, s, —CH$_2$—) 4.23–3.90 (5H, m, C$_3'$,4',5'—H, COCH) 2.30–2.17 (2H, m, C$_2'$—H) 1.36–1.20 (12H, m, CH$_3$ × 4) |

TABLE 4-continued

| Ex. No. | R¹ | R² | Yield (%) | Form | NMR (DMSO-$d_6$), δ |
|---|---|---|---|---|---|
| 13 | —CH₂-(furan) | NHCOCH₂-Ph / —C(=O)—CH(CH₂)₄NHCOCH₂-Ph (L) | 40 | Powder | 9.02 (1H, bs, N₃—H) 7.48 ((1H, d, J=6Hz, C₆—H) 7.41 (1H, t, J=1Hz, -Ph(×2)-CH₂) 7.31 (10H, s, —CH₂-Ph) 6.34 (2H, d, J=1Hz, —CH₂-furan) |
| 14 | —CH₂-(furan) | NHCOCH₂-Ph / —C(=O)—CHCH₂-Ph-OCH₂-Ph (L) | 50 | Powder | 11.86 (1H, d, N₃—H) 7.90–7.75 (2H, m, C₆—H, NH) 7.64–7.61 (1H, m, -Ph(×2)-CH₂) 7.46–7.29 (10H, m, CH₂-Ph) 7.16 (2H, d, J=9Hz, —O-Ph-CH₂) 6.90 (2H, d, J=9Hz, |

(Note: additional NMR peaks for Ex. 13: 6.08–6.00 (1H, m, C₁′—H) 5.52 (1H, bs, NH) 5.08 (4H, s, —CH₂-Ph × 2) 4.88 (1H, bs, NH) 4.46 (2H, s, —CH₂-furan) 4.31–4.05 (5H, m, C₃′,4′,5′—H, COCH) 3.27–3.05 (2H, m, NHCH₂) 2.50–1.20 (8H, m, C₂′—H, CHCH₂CH₂CH₂))

TABLE 4-continued

| Ex. No. | R¹ | R² | Yield (%) | Form | NMR (DMSO-d$_6$): δ |
|---|---|---|---|---|---|
| 15 | —CH$_2$-(furan) | NHCOCH$_2$-Ph / —C(=O)—CH(CH$_2$)$_2$COCH$_2$-Ph (L) | 98 | Powder | —CH$_2$-(methoxy-dimethylphenyl) 6.43–6.42 (2H, m, —CH$_2$) 6.15–6.01 (1H, m, C$_1$′—H) 5.05 & 4.97 (each, 2H, s, —CH$_2$-Ph) 4.45 (2H, s, —CH$_2$-furan) 4.28–4.02 (5H, m, C$_3$′, 4′, 5′—H, COCH) 2.94–2.88 (2H, m, CH—CH$_2$) 2.24–2.15 (2H, m, C$_2$′—H); 11.80 (1H, bs, N$_3$—H) 7.90–7.74 (2H, m, C$_6$—H, NH) 7.64–7.62 (1H, m, —CH$_2$-dimethylphenyl ×2) 7.33 (10H, s, CH$_2$-Ph ×2) 6.43–6.42 (2H, m, —CH$_2$-furan) 6.10–5.98 (1H, m, C$_1$′—H) 5.07 and 5.01 (each 2H, s, —CH$_2$-Ph ×2) 4.47 (2H, s, —CH$_2$-furan) 4.22–4.12 (5H, m, C$_3$′, 4′, 5′—H, COCH) 2.54–2.31 (m, CHCH$_2$, coalesced with DMSO) 2.22–1.64 (4H, m, C$_2$′—H, COCH$_2$) |
| 16 | —CH$_2$-(ethylthiophene) | —CCH$_2$NHCOC(CH$_3$)$_3$ (O,O) | 63 | Hygroscopic powder | 11.85 (1H, bs, N$_3$—H) 7.92 (1H, d, J=7Hz, C$_6$—H) 7.20 (1H, bs, NH) 6.88 & 6.70 (each, 1H, d, J=4Hz, —CH$_2$-(ethylthiophene)-C$_2$H$_5$) 6.18–6.02 (1H, m, C$_1$′—H) |

TABLE 4-continued

| Ex. No. | R¹ | R² | Yield (%) | Form | NMR (DMSO-d$_6$): δ |
|---|---|---|---|---|---|
| 17 | —CCH$_2$NHCOC(CH$_3$)$_3$ with two =O | —CH$_2$— thiophene —Cl | 81 | Hygroscopic powder | 4.63 (2H, s, —CH$_2$—C$_2$H$_5$) 4.22–4.09 (4H, m, C$_3'$, 4', 5'—H) 3.70 (2H, d, J=6Hz, COCH$_2$) 2.78 (2H, q, J=7Hz, CH$_2$CH$_3$) 2.33–2.18 (2H, m, C$_2'$—H) 1.37 (9H, s, C(CH$_3$)$_3$) 1.22 (3H, t, J=7Hz, CH$_2$CH$_3$) 11.84 (1H, bs, N$_3$—H) 7.90 (1H, d, J=7Hz, C$_6$—H) 7.22 (1H, t, J=6Hz, NH) 7.03–6.93 (2H, m, —CH$_2$— thiophene —H) 6.24–6.08 (1H, m, C$_1'$—H) 5.26–5.24 (1H, m, C$_4'$—H) 4.68 (2H, s, —CH$_2$—Cl) 4.15–4.13 (1H, m, C$_4'$—H) 3.75–3.69 (4H, m, C$_5'$—H, COCH$_2$) 2.35–2.23 (2H, m, C$_2'$—H) 1.39 (9H, s, CH$_3$ × 3) |
| 18 | —CH$_2$— thiophene with Br, Br | —CCH$_2$NHCOC(CH$_3$)$_3$ with two =O | 67 | Hygroscopic powder | 9.24 (1H, bs, N$_3$—H) 7.60 (1H, d, J=6Hz, C$_6$—H) 6.84 (1H, s, —CH$_2$— thiophene —Br) 6.24–6.07 (1H, m, C$_1'$—H) 5.09 (1H, bs, NH) 4.59 (2H, s, —CH$_2$— thiophene —Br) 4.40–4.32 (2H, m, C$_3'$, 4'—H) 4.19–4.06 (2H, m, C$_5'$—H) 3.93 (2H, d, J=6Hz, COCH$_2$) 2.60–1.98 (2H, m, C$_2'$—H) 1.44 (9H, s, CH$_3$ × 3) |

EXAMPLE 19

Preparation of 5'-O-β-alanyl-3'-O-(5-chloro-2-thenyl)-2'-deoxy-5-fluorouridine hydrochloride To 0.82 g of 5'-O-[N-(t-butoxycarbonyl)-β-alanyl]3'-O-(5-chloro-2-thenyl)-2'-deoxy-5-fluorouridine obtained in Example 7 was added 10 ml of 4N hydrochloric acid-dioxane, and the mixture was stirred at room temperature for 30 minutes.

The reaction mixture was concentrated under reduced pressure and the residue was washed with hot ethyl acetate, giving 0.69 g of the desired 5'-O-β-alanyl-3'-O-(5-chloro-2-thenyl)-2'-deoxy-5-fluorouridine hydrochloride.

Yield: 95%.
Form : Hygroscopic powder.
Elemental analysis for $C_{17}H_{19}ClFN_3O_6S \cdot HCl \cdot 2.5 H_2O$:
Calcd.: C., 38.57%; H, 4.76%; N, 7.94%.
Found : C., 38.56%; H, 5.12%; N, 7.61%.
NMR (DMSO-$d_6$) δ:
11.85 (1H, bs, $N_3$-H),
8.24-7.88 (4H, m, $C_6$-H, $NH_2$·HCl),
7.05-6.95 (2H, m,

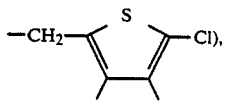

6.17-6.03 (1H, m, $C_{1'}$-H), 4.67 (2H, s

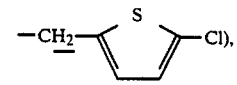

4.35-4.20 (4H, m, $C_{3', 4', 5'}$-H),
3.18-2.97 (2H, m, $CH_2NH_2$),
2.75 (2H, t, J=6Hz, $COCH_2$), 2.37-2.25 (2H, m, $C_{2'}$-H).

EXAMPLES 20-23

Following the general procedure of Example 19 and using appropriate starting materials, the compounds having the following structural formula and shown in Table 5 below were prepared.

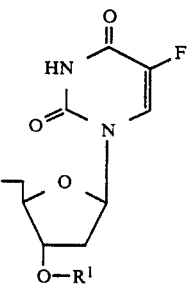

TABLE 5

| Ex. No. | $R^1$ | $R^2$ | Yield (%) | Form | NMR (DMSO-$d_6$): δ |
|---|---|---|---|---|---|
| 20 | —CH₂—(5-Cl-thienyl) | —C(O)—CHCH(CH₃)₂ with NH₂·HCl (L) | 28 | Hygroscopic powder | 8.62 (3H, bs, NH₂, HCl) 7.99 (1H, d, J=7Hz, $C_6$—H) 7.07-6.98 (2H, m, —CH₂—(thienyl)—Cl) 6.21-6.06 (1H, m, $C_1'$—H) 4.69 (2H, s, —CH₂—(thienyl)—Cl) 4.40-4.14 (4H, m, $C_{3', 4', 5'}$—H) 3.85 (1H, d, J=5Hz, COCH) 2.28-1.99 (3H, m, $C_{2'}$—H, CH(CH₃)₂) 0.86 and 0.82 (each 2H, d, J=7Hz, CH₃) |
| 21 | —CH₂—(5-Cl-thienyl) | —C(O)—CH(CH₂)₂SCH₃ with NH₂·HCl | 47 | Hygroscopic powder | 11.89 (1H, bs, $N_3$—H) 8.77 (3H, bs, NH₂, HCl) 7.99 (1H, d, J=7Hz, $C_6$—H) 7.04-6.95 (2H, m, —CH₂—(thienyl)—Cl) 6.20-6.05 (1H, m, $C_1'$—H) 6.20-6.05 (1H, m, $C_1'$—H 4.69 (2H, s, —CH₂—(thienyl)—Cl) 4.50-4.05 (5H, m, $C_{3', 4', 5'}$—H, COCH) 2.71-2.47 (m, coalesced with DMSO, COCHCH₂) 2.44-2.02 (7H, m, $C_{2'}$—H, CH₂SCH₃) |
| 22 | —CH₂—(5-Cl-thienyl) | —C(O)—CHCH₃ with NH₂·HCl (D) | 36 | Hygroscopic powder | 11.80 (1H, bs, $N_3$—H) 8.58 (3H, bs, NH₂, HCl) 7.98 (1H, d, J=7Hz, $C_6$—H) 6.99-6.84 (2H, m, —CH₂—(thienyl)—Cl) |

TABLE 5-continued

| Ex. No. | R¹ | R² | Yield (%) | Form | NMR (DMSO-d₆): δ |
|---|---|---|---|---|---|
| | | | | | 6.11–5.97 (1H, m, $C_1'$—H) 4.68 (2H, s, —CH₂-[thiophene]-Cl) 4.38–3.94 (5H, m, $C_{3',4',5'}$—H, COCH) 2.39–2.27 (2H, m, $C_2'$—H) 1.42 (3H, d, J=7Hz, CH₃) |
| 23 | 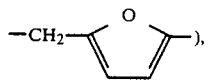 | 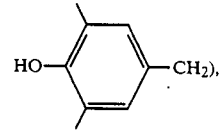 | 49 | Hygroscopic powder | 8.89 (3H, bs, NH₂, HCl) 7.92 (1H, d, J=7Hz, $C_6$—H) 7.04–6.95 (2H, m, —CH₂-[thiophene]-Cl) 6.29–6.14 (1H, m, $C_1'$—H) 5.36–5.31 (1H, m, $C_3'$—H) 4.69 (2H, s, —CH₂-[thiophene]-Cl) 4.25–4.23 (1H, m, $C_4'$—H) 3.83 (2H, s, COCH₂) 3.73–3.60 (2H, m, $C_5'$—H) 2.42–2.31 (2H, m, $C_2'$—H) |

EXAMPLE 24

Preparation of 2'-deoxy-5-fluoro-3'-O-furfuryl-5'-O-L-tyrosyluridine

To a solution of 1.10 g of 5'-O-(O-benzyl-N-benzyloxycarbonyl-L-tyrosyl)-2'-deoxy-5-fluoro-3'-O-furfuryluridine prepared in Example 14 in 50 ml of methanol was added 0.11 g of 5% palladium-carbon, and the mixture was stirred in a hydrogen stream under ambient temperature and pressure condition for 2 hours. The catalyst was filtered off, and the solvent was evaporated off under reduced pressure. The residue was placed on silica gel column and eluted with 5% methanol-chloroform for purification, thereby giving 0.13 g of 2'-deoxy-5-fluoro-3'-O-furfuryl-5'-O-L-tyrosyluridine. Yield: 17%.

Form : Hygroscopic powder.
Elemental analysis: for $C_{23}H_{24}FN_3O_8 \cdot 1.5H_2O$:
Calcd.: C., 53.49%; H, 5.27%; N, 8.14%.
Found : C., 53.86%; H, 5.58%; N, 7.78%.
NMR (DMSO d₆) δ:
7.91 (1H, d, J=7Hz, $C_6$-H),
7.65-7.62 (1H, m,

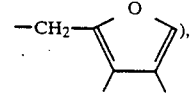

6.96 (2H, d, J=9Hz,

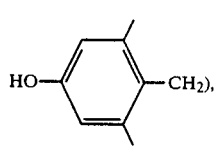

6.64 (2H, d, J=9Hz, 6.47-6.39 (2H, m,

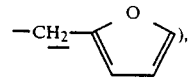

6.16-5.98 (1H, m, $C_1'$-H), 5.03 (1H, bs, OH), 4.45 (2H, s, 4.13-3.94 (5H, m, $C_{3',4',5'}$-H, COCH),
3.61-3.41 (2H, m, NH₂), 2.72 (2H, d, J=7Hz, CHCH₂),
2.23-2.10 (2H, m, $C_2'$-H).

EXAMPLE 25

Following the general procedure of Example 24 and using appropriate starting materials, the compounds having the following structural formula and shown in Table 6 below were prepared.

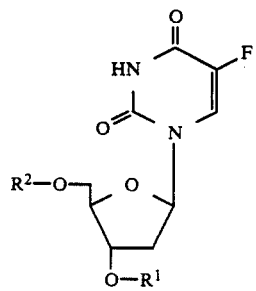

TABLE 6

| Ex. No. | R¹ | R² | Yield (%) | Form | NMR (DMSO-$d_6$): δ |
|---|---|---|---|---|---|
| 25 | —CH₂-(furan) | —C(=O)—CH(NH₂)(CH₂)₄NH₂ (L) | 49 | Hygroscopic powder | 7.85 (1H, d, J=7Hz, $C_6$—H)<br>7.68–7.63 (1H, m, —CH₂-(furan))<br>7.50–7.41 (2H, m, —CH₂-(furan))<br>6.18–6.03 (1H, m, $C_{1'}$—H)<br>5.23 (4H, bs, NH₂ × 2)<br>4.50 (2H, s, —C$\underline{H}_2$-(furan))<br>4.26–3.87 (5H, m, $C_{3',4',5'}$—H, COCH)<br>3.45–3.32 (2H, m, C$\underline{H}_2$NH)<br>2.82–2.69 (2H, m, C$\underline{H}$CH₂)<br>2.32–2.20 (2H, m, $C_{2'}$—$\underline{H}$)<br>1.50–1.30 (4H, m, H₂NCH₂C$\underline{H}_2$C$\underline{H}_2$) |

EXAMPLE 26

Preparation of 3'-O-(5-chloro-2-thenyl)-2'-deoxy-5'-O-[3(diethylamino)propanoyl]-5-fluorouridine 2,4,6-triisopropylbenzenesulfonate To a solution of 1.00 g of 3'-O-(5-chloro-2- thenyl)-2'-deoxy-5-fluorouridine in 50 ml of pyridine were added 0.72 g of N,N-diethyl-β-alanine hydrochloride and 1.61 g of triisopropylbenzenesulfonyl chloride, and the mixture was stirred at room temperature for 1 day. The reaction mixture was concentrated under reduced pressure, and the residue was placed on silica gel column and eluted with 2% methanol-chloroform for purification, thereby giving 0.97 g of 3'-O-(5-chloro-2-thenyl)-2'-deoxy-5'-O- [3-(diethylamino)propanoyl]-5-fluorouridine 2,4,6-triisopropylbenzenesulfonate.

Yield: 46%.
Form : Hygroscopic powder.
Elemental analysis: for C₂₁H₂₇ClFN₃O₆S·C₁₅H₂₃SO₃H·H₂O:
Calcd.: C., 53.62%; H, 6.62%; N, 5.21%.
Found : C., 53.43%; H, 6.51%; N, 4.93%.
NMR (DMSO-$d_6$) δ:
11.92 (1H, d, NH), 8.92 (1H, bs, SO₃H),
7.95 (1H, d, J=7Hz, $C_6$-H)
7.05–6.59 (4H, m, 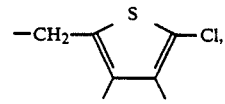

6.20-6.02 (1H, m, $C_{1'}$-H), 4.72-4.42 (4H, m,

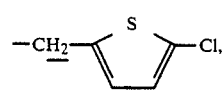

4.30-3.54 (9H, m, 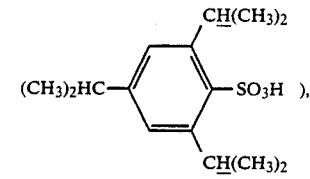

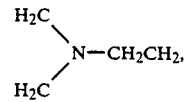

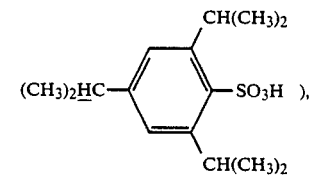

2.35-2.21 (2H, m, $C_{2'}$-H), 1.27-1.07 (24H, m, CH₃ ×8).

EXAMPLE 27

Preparation of 5'-O-[N-(t-butoxycarbonyl)-L-prolyl]-3'-O-(5-chloro-2-thenyl)-2'-deoxy-5-fluorouridine To a solution of 2.29 g of N-(t-butoxycarbonyl)- L-proline in 50 ml of acetonitrile was added 1.31 g of 1,3-dicyclohexylcarbodiimide, and the mixture was stirred with ice-cooling for 1.5 hours.

The reaction mixture was filtered and concentrated. To the residue were added 50 ml of pyridine and 1.00 g of 3'-O-(5-chloro-2-thenyl)-2'-deoxy-5fluorouridine, and the mixture was subjected to reaction at room temperature for 17 hours. The solvent was evaporated and the residue was dissolved in 30 ml of ethyl acetate. The solution was washed with water, dried and concentrated. The residue was placed on silica gel column and eluted with chloroform for purification, thereby giving 1.21 g of the desired 5'-O-[N-(t-butoxycarbonyl)-L-prolyl]-3'-O-(5-chloro-2-thenyl)-2'deoxy-5-fluorouridine.

Yield: 80%.
Form : Hygroscopic powder.
Elemental analysis for $C_{24}H_{29}ClFN_3O_8S\cdot 2H_2O$:
Calcd.: C., 47.25%; H, 5.45%; N, 6.89%.
Found : C., 46.81%; H, 5.06%; N, 6.55%.
IR : KBr $\nu_{C=O}(cm^{-1})$ : 1750, 1718, 1665.

EXAMPLE 28

Preparation of 3'-O-(5-chloro-2-thenyl)-2'-deoxy-5-fluoro-5'-O-L-prolyluridine hydrochloride To 1.21 g of 5'-O-[N-(t-butoxycarbonyl)-L- prolyl]-3'-O-(5-chloro-2-thenyl)-2'-deoxy-5-fluorouridine prepared in Example 27 was added 20 ml of 4N hydrochloric acid-dioxane, and the mixture was stirred at room temperature for 30 minutes.

The reaction mixture was concentrated under reduced pressure, and the residue was washed with hot ethyl acetate, giving 0.88 g of the desired 3'-O-(5- chloro-2-thenyl)-2'-deoxy-5-fluoro-5'-O-L-prolyluridine hydrochloride.

Yield: 82%.
Form : Hygroscopic powder.
Elemental analysis: for $C_{19}H_{21}ClFN_3O_6S\cdot HCl\cdot 1.5-H_2O$:
Calcd.: C., 42.47%; H, 4.69%; N, 7.82%.
Found : C., 42.17%; H, 5.05%; N, 7.64%.
NMR (DMSO-d6) δ:
11.86 (1H, bs, $N_3$-H), 9.79 (2H, bs, NH, HCl),
7.99 (1H, d, J=7Hz), $C_6$-H),
7.05-6.97 (2H, m,

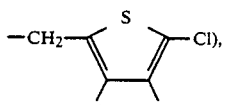

6.20-6.02 (1H, m, $C_{1'}$-H 4.69 (2H, s,

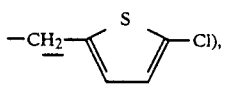

4.46-4.13 (5H, m, $C_{3',4',5'}$-H, COCH),
3.26 (2H, t, J=7Hz, CH$_2$NH),
2.37-1.79 (6H, m, $C_{2'}$-H, NHCH$_2$CH$_2$CH$_2$)

EXAMPLE 29

Preparation of 5'-O-N-(benzyloxycarbonylglycyl)-2'-deoxy- 5-fluoro 3'-O-furfuryluridine To a solution of 1.00 g of 2'-deoxy-5-fluoro-3'-O-furfuryluridine in 50 ml of pyridine was added 1.39 g of N-benzyloxycarbonylglycyl chloride, and the mixture was subjected to reaction at room temperature overnight.

The solvent was distilled off and the residue was dissolved in 30 ml of ethyl acetate The solution was washed with water, dried and concentrated. The residue was placed on silica gel column and eluted with 1% methanol-chloroform for purification, giving 0.32 g (20%) of the desired 5'-O-(N-benzyloxycarbonylglycyl)-2'-deoxy- 5-fluoro-3'-O-furfuryluridine.

Form : Powder.
Elemental analysis for $C_{24}H_{24}FN_3O_9$:
Calcd.: C., 55.71%; H, 4.68%; N, 8.12%.
Found : C., 55.34%; H, 5.01%; N, 7.98%.
NMR (DMSO-d6) δ:
11.84 (1H, bd, $N_3$-H), 7.90 (1H, d, J=7Hz, $C_6$-H),
7.72-7.63 (2H, m. NH,

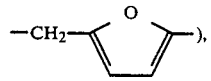

7.34 (5H, s,

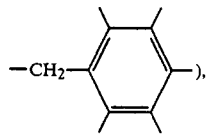

6.44-6.34 (2H, m,

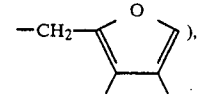

6.10-5.95 (1H, m, $C_{1'}$-H), 5.04 (2H, s,

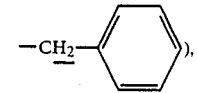

4.48 (2H, s,

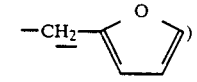

4.27-4.10 (4H, m, $C_{3',4',5'}$-H),
3.82 (2H, d, J=6Hz COCH$_2$), 2.30-2.17 (2H, m, $C_{2'}$-H).

EXAMPLE 30

Preparation of 3'-O-(5-carboxyfurfuryl)-2'-deoxy-5-fluorouridine and 5'-O-[N-(t-butoxycarbonyl)glycyl]-3'-O-(5-carboxyfurfuryl)-2'-deoxy-5-fluorouridine To a solution of 5.00 g of 2'-deoxy-5-fluoro-5'-O-trityluridine in 100 ml of dioxane were added 5.74 g of fine powder of potassium hydroxide and 2.67 g of 5-methoxycarbonylfurfuryl chloride, and the mixture was stirred at temperature of 80° C. for 2.5 hours. The reaction mixture was concentrated and the residue was dissolved in 100 ml of water. The reaction mixture was adjusted to a pH of 4 with one normal hydrochloric acid and then extracted with ethyl acetate. The organic layer was dried and concentrated To the residue was added 100 ml of 80% acetic acid The mixture was left to stand at a temperature of 80° C. for one hour. The solvent was distilled off and the residue was washed with ethyl acetate and methanol, giving 2.53 g (67%) of 3'-O-(5carboxyfurfuryl)-2'-deoxy-5-fluorouridine.

Form : Hygroscopic powder.
Elemental analysis: for $C_{15}H_{15}FN_2O_8 \cdot H_2O$:
Calcd.: C., 46.40%; H, 4.41%; N, 7.21%.
Found : C., 46.32%; H, 4.56%; N, 7.13%.
NMR (DMSO-$d_6$) δ:
12.68 (1H, bs, COOH), 11.76 (1H, bd, NH),
8.18 (1H, d, J=7Hz, $C_6$-H),
7.17 (1H, d, J=4Hz,

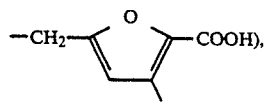

6.62 (1H, d, J=4Hz,

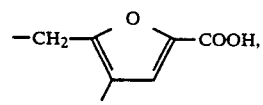

6.12-5.98 (1H, m, $C_{1'}$-H), 4.77 (1H, bs, $C_{5'}$-OH),
4.56 (2H, s,

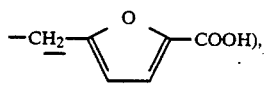

4.19-4.12 (1H, m, $C_{3'}$-H), 3.99-3.88 (1H, m, $C_{4'}$-H),
3.60 (2H, bs, $C_{5'}$-H), 2.29-2.06 (2H, m, $C_{2'}$-H)

Subsequently, 0.84 g of 1,3-dicyclohexylcarbodiimide was added to a solution of 1.19 of N-(t-butoxycarbonyl)glycine in 30 ml of acetonitrile, and the mixture was stirred with ice-cooling for one hour.

The reaction mixture was filtered and concentrated. To the residue were added 30 ml of pyridine and 0.63 g of 3'-O-(5-carboxyfurfuryl)-2'-deoxy-5-fluorouridine. The mixture was subjected to reaction at room temperature for 2 hours. The solvent was distilled off and the residue was placed on silica gel column and eluted with 5% methanol-chloroform for purification giving 0.59 g of the desired 5'-O-[N-(t-butoxycarbonyl)glycyl]-3'O-(5-carboxyfurfuryl)-2'-deoxy-5-fluorouridine.

Yield 66%.
Form Hygroscopic powder.
Elemental analysis: for $C_{22}H_{26}FN_3O_{11} \cdot H_2O$:
Calcd.: C., 48.44%; H, 5.17%; N, 7.70%.
Found : C., 48.03%; H, 5.35%; N, 7.68%.
NMR (DMSO-$d_6$) δ:
11.83 (1H, bs, $N_3$-H), 7.92 (1H, d, J=7Hz, $C_6$-H),
7.24-7.14 (2H, m, NH

6.62 (1H, d, J=4Hz,

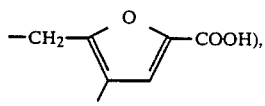

6.15-5.98 (1H, m, $C_{1'}$-H),
4.57 (2H, s,

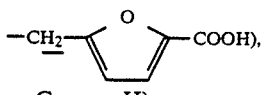

4.28-4.14 (4H, m, $C_{3'}$, $_{4'}$, $_{5'}$-H),
3.72 (2H, d, J=6Hz, COCH$_2$), 2.28-2.17 (2H, m, $C_{2'}$-H),
1.37 (9H, s, CH$_3$ ×3).

EXAMPLE 31

Preparation of
2'-deoxy-5-fluoro-3'-O-(3,4,5-tribromo-2-thenyl)uridine
and 5'-O-[N-(t-butoxycarbonyl)glycyl]-2'-deoxy-5-fluoro-3'-O-(3,4,5-tribromo-2-thenyl)uridine To a solution of 5.00 g of 2'-deoxy-5-fluoro-5'-O-trityluridine in 100 ml of dioxane were added 5.74 g of fine powder of potassium hydroxide and 5.65 g of 2,3,4-tribromo-5-chloromethylthiophene, and the mixture was stirred at a temperature of 80° C. for 2 hours. The reaction mixture was concentrated and the residue was dissolved in 100 ml of ethyl acetate. The solution was washed with aqueous solution of acetic acid, dried and concentrated. To the residue was added 100 ml of 80% acetic acid and the mixture was left to stand at a temperature of 80° C. for one hour. The solvent was distilled off and the residue was placed on silica gel column and eluted with 2% methanol-chloroform for purification, giving 1.07 g (18%) of the desired 2'-deoxy 5-fluoro-3'-O-(3,4,5-tribromo-2-thenyl)uridine.

Form : Powder.
Elemental analysis: for $C_{14}H_{12}FN_2O_5S$:
Calcd.: C., 29.04%; H, 2.09%; N, 4.84%.
Found : C., 29.00%; H, 2.25%; N, 4.38%.
NMR (DMSO-$d_6$) δ:
11.81 (1H, d, J=5Hz, NH), 8.18 (1H, d, J=7Hz, $C_6$-H),
6.16-6.01 (1H, m, $C_{1'}$-H), 5.21 (1H, bs, $C_{5'}$-OH),
4.71 (2H, s,

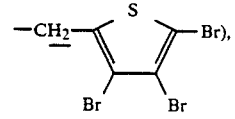

(4.29-4.24 (1H, m, $C_{3'}$-H)
4.03-4.01 (1H, m, $C_{4'}$-H), 3.62 (2H, bs, $C_{5'}$-H)
2.35-2.25 (2H, m, $C_{2'}$-H)

Subsequently, to a solution of 1.21 g of N-(t-butoxycarbonyl)glycine in 50 ml of acetonitrile was added 0.86 g of 1,3-dicyclohexylcarbodiimide, and the mixture was stirred with ice-cooling for one hour. The reaction mixture was filtered and concentrated. To the residue were added 50 ml of pyridine and 1.00 g of 2'-deoxy-5-fluoro-3'-O-(3,4,5-tribromo-2-thenyl)uridine, and the mixture was subjected to reaction at room temperature for 2 hours. The solvent was distilled off and the residue was dissolved in 50 ml of ethyl acetate. The solution was washed with saturated aqueous solution of sodium hydrogen carbonate and saturated aqueous solution of sodium chloride, dried over anhydrous sodium sulfate and the solvent was distilled off. The resulting residue was placed on silica gel column and eluted with 1% methanolchloroform for purification, giving 1.00 g (79%) of the desired 5'-O-[N-(t-butoxycarbonyl)-glycyl]-2'-deoxy-5-fluoro-3'-O-(3,4,5-tribromo-2-thenyl)uridine.

Form Powder.
Elemental analysis: for $C_{21}H_{23}Br_3FN_3O_8S$.
Calcd.: C., 34.26%; H, 3.15%; N, 5.71%.
Found : C., 34.41%; H, 3.22%; N, 5.56%.
NMR (DMSO-$d_6$) δ:
11.86 (1H, d, J=5Hz, $N_3$-H),
7.93 (1H, d, J=7Hz, $C_6$-H), 7.20 (1H, bt, NH),
6.18-6.02 (1H, m, $C_{1'}$-H), 4.72 (2H, s,

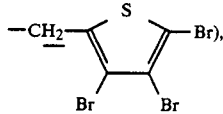

4.27-4.15 (4H, m, $C_{3',4',5'}$-H),
3.72 (2H, d, J=6Hz, COCH$_2$), 2.40-2.27 (2H, m, $C_{2'}$-H),
1.37 (9H, s, CH$_3$ ×3).

Then the above product was treated in 4N hydrochloric acid-dioxane mixture in the same manner as in Example 1, giving 2'-deoxy-5-fluoro-5'-O-glycyl-3'-O-(3,4,5-tribromo-2-thenyl)uridine hydrochloride.

Form : Hygroscopic powder.
Yield: 96%.
Elemental analysis for $C_{16}H_{15}Br_3FN_3O_6S\cdot HCl\cdot H_2O$:
Calcd.: C., 27.83%; H, 2.63%; N, 6.08%.
Found : C., 27.51%; H, 2.82%; N, 5.94%.
NMR (DMSO-$d_6$) δ:
11.86 (1H, bs, $N_3$-H), 8.41 (3H, bs, NH$_2$, HCl),
7.99 (1H, d, J=7Hz, $C_6$-H), 6.21-6.07 (1H, m, $C_{1'}$-H), 4.73 (2H, s,

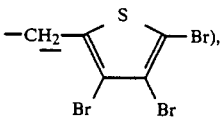

4.42-4.15 (4H, m, $C_{3',4',5'}$-H), 3.84 (2H, bs, COCH$_2$), 2.54-2.37 (m, $C_{2'}$-H, coalesced with DMSO).

EXAMPLE 32

Preparation of 2'-deoxy-3'-O-(4,5-dichloro-2-thenyl)-5-fluorouridine, 5'-O-[N-(t-butoxycarbonyl)glycyl]-2'-deoxy-3'-O-(4,5-dichloro-2-thenyl)-5-fluorouridine and 2'-deoxy-3'-O-(4,5-dichloro-2-thenyl)-5-fluoro-5'-O-glycyluridine hydrochloride To a solution of 5.00 g of 2'-deoxy-5-fluoro-5'-O-trityluridine in 100 ml of dioxane were added 2.50 g of fine powder of potassium hydroxide and 2 50 g of 2 3-dichloro-5-chloromethylthiophene, and the mixture was stirred at a temperature of 80° C. for 2 hours. The reaction mixture was concentrated and the residue was dissolved in 100 ml of ethyl acetate. The solution was washed with aqueous solution of acetic acid, dried and concentrated. To the residue was added 100 ml of 80% acetic acid and the mixture was left to stand at a temperature of 80° C. for one hour. The solvent was distilled off and the residue was placed on silica gel column and eluted with 2% methanol-chloroform for purification, giving 3.12 g (74%) of the desired 2'-deoxy- 3'-O-(4,5-dichloro-2-thenyl)-5-fluorouridine.

M.p. : 147–149° C.
NMR (DMSO-$d_6$) δ:
11.81 (1H, bd, NH), 8.18 (1H, d, J=7Hz, $C_6$-H),
7.12 (1H, s,)

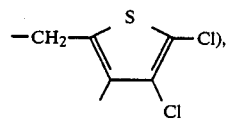

6.18-6.04 (1H, m, $C_{1'}$-H),
5.20 (1H, bs, $C_{5'}$-H), 4.70 (2H, s,

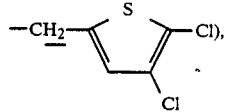

4.22 (1H, bs, $C_{3'}$-H), 4.01 (1H, bs, $C_{4'}$-H),
3.61 (2H, bs, $C_{5'}$-H), 2.29-2.16 (2H, m, $C_{2'}$-H).

Subsequently, to a solution of 0.66 g of N-(t-butoxycarbonyl)glycine in 30 ml of acetonitrile was added 0.47 g of 1,3-dicyclohexylcarbodiimide, and the mixture was stirred with ice-cooling for 2 hours. The reaction mixture was filtered and concentrated. To the residue were added 30 ml of pyridine and 0.36 g of 2'deoxy-3'-O-b (4,5-dichloro-2-thenyl)-5-fluorouridine, and the mixture was subjected to reaction at room temperature for 12 hours. The solvent was distilled off and the residue was dissolved in 30 ml of ethyl acetate. The solution was washed with saturated aqueous solution of sodium hydrogen carbonate and saturated aqueous solution of sodium chloride, dried over anhydrous magnesium sulfate and the solvent was distilled off. The resulting residue was placed on silica gel column and eluted with 1% methanolchloroform for purification, giving 0.36 g (72%) of the desired 5'-O-[N-(t-butoxycarbonyl)-glycyl]-2'-deoxy-3'-O- (4,5-dichloro-2-thenyl)-5-fluorouridine.

Form : Powder.
NMR (DMSO-$d_6$) δ:
11.86 (1H, bd, $N_3$-H), 7.92 (1H, d, J=7Hz, $C_6$-H),
7.29-7.12 (2H, m, NH,

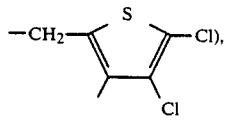

6.21-6.07 (1H, m, $C_{1'}$-H), 4.67 (2H, s,

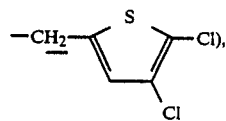

4.31-4.12 (4H, m, $C_{3',4',5'}$-H), 3.72 (2H, d, J=6Hz, COCH$_2$), 2.36-2.24 (2H, m, $C_{2'}$-H), 1.37 (9H, s, CH$_3$ ×3).

Then the above product was treated in 4N hydrochloric acid-dioxane mixture in the same manner as in Example 19, giving 0.28 g (96%) of the desired 2'-deoxy 3'-O-(4,5-dichloro-2-thenyl)-5-fluoro-5'-O-glycyluridine hydrochloride.

Form : Hygroscopic powder.

NMR (DMSO-d$_6$) δ:

11.86 (1H, bs, N$_3$-H), 8.73 (3H, bs, NH$_2$, HCl), 8.03 (1H, d, J=7Hz, C$_6$-H), 7.17 (1H, s,

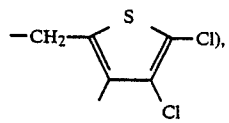

6.21-6.08 (1H, m, C$_1'$-H), 4.71 (2H, s,

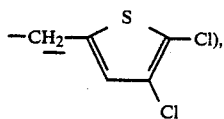

4.41-4.16 (4H, m, $C_{3',4',5'}$-H), 3.83 (2H, bs, COCH$_2$) 2.42-2.32 (2H, m, $C_{2'}$-H).

Pharmacological Test 1

Sarcoma-180 subcultured in ascites of ICR mice was diluted with a physiological saline and subcutaneously transplanted into the backs of ICR mice in an amount of 2 ×10$^7$ cells each. Twenty-four hours after the transplantation, a test compound dissolved in sterilized physiological saline was administered to the tail vein of each of the mice once a day for 7 consecutive days.

The solid tumor was isolated from under the dorsal skin of mice on the 10th day after the transplantation to measure the weight of the tumor There was determined the ratio (T/C) of the weight of tumor (T) of the test compound group to the weight of tumor (C) of the control group. The 50% tumor inhibition dose (ED$_{50}$ value) in which T/C is 0.5 was determined from the dose-response curve of dosage and the ratio (T/C). Table 7 shows the results.

Test Compound 1:
3'-O-(5-chloro-2-thenyl)-2'-deoxy-5-fluoro-5'-O-glycyluridine hydrochloride Test Compound 2:
3'-O-(5-bromo-2-thenyl)-2'-deoxy-5-fluoro-5'-O-glycyluridine hydrochloride Test Compound 3:
5'-O-D-alanyl-3'-O-(5-chloro-2-thenyl)-2'-deoxy-5-fluorouridine hydrochloride Test Compound 4:
5'-O-(5-chloro-2-thenyl)-2'-deoxy-5-fluoro-3'-O-glycyluridine hydrochloride

TABLE 7

| Test Compound | ED$_{50}$ (mg/kg) |
|---|---|
| 1 | 5 |
| 2 | 5 |
| 3 | 7 |
| 4 | 7 |

Preparation Example 1

| Final compound of Example 1 | 50 mg |
|---|---|
| Lactose | 97 mg |
| Crystalline cellulose | 50 mg |
| Magnesium stearate | 3 mg |

Capsules (200 mg each) were prepared which each had the foregoing composition.

Preparation Example 2

| Final compound of Example 4 | 10 mg |
|---|---|
| Lactose | 184 mg |
| Crystalline cellulose | 100 mg |
| Magnesium stearate | 6 mg |

Capsules (300 mg each) were prepared which each had the foregoing composition.

Preparation Example 3

| Compound of Example 6 | 10 mg |
|---|---|
| Lactose | 240 mg |
| Corn starch | 340 mg |
| Hydroxypropyl cellulose | 10 mg |

Granules (600 mg each wrapper) were prepared which each had the foregoing composition.

Preparation Example 4

| Compound of Example 2 | 10 mg |
|---|---|
| Macrogol 300 | 500 mg |
| Distilled water for injection | (appropriately) |

An injection solution (5ml per ampul) was prepared which had the foregoing composition.

We claim:

1. A 2'-deoxy-5fluorouridine compound of the formula

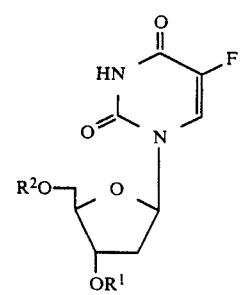

wherein:

R$^1$ is a furanylmethyl or thienylmethyl group which may be substituted by 1 to 3 halogen atoms on the furan or thiophene ring; and $R^2$ is a lower alkanoyl group which may be substituted by one —$NH_2$ group; or a salt thereof.

2. A compound as defined in claim 1 wherein $R^1$ is a thienyl-lower alkyl group which has 1 to 3 halogen atoms as the substituent on the thiophene ring.

3. A compound as defined in claim 1 wherein $R^1$ is a furanyl-lower alkyl group which has 1 to 3 halogen atoms as the substituents on the furan ring.

4. A compound as defined in claim 2 wherein $R^1$ is a thienyl-lower alkyl group which has one halogen atom as the substituent on the thiophene ring.

* * * * *